(12) United States Patent
Ostrand-Rosenberg et al.

(10) Patent No.: US 8,444,965 B2
(45) Date of Patent: *May 21, 2013

(54) TUMOR CELLS FROM IMMUNE PRIVILEGED SITES AS BASE CELLS FOR CELL-BASED CANCER VACCINES

(75) Inventors: Suzanne Ostrand-Rosenberg, Columbia, MD (US); Jacobus J. Bosch, Baltimore, MD (US); Bruce R. Ksander, Belmont, MA (US)

(73) Assignee: University of Maryland, Baltimore County, Baltimore, MD (US)

( * ) Notice: Subject to any disclaimer, the term of this patent is extended or adjusted under 35 U.S.C. 154(b) by 273 days.

This patent is subject to a terminal disclaimer.

(21) Appl. No.: 12/889,043

(22) Filed: Sep. 23, 2010

(65) Prior Publication Data

US 2011/0165187 A1  Jul. 7, 2011

Related U.S. Application Data

(63) Continuation of application No. 12/015,116, filed on Jan. 16, 2008, now Pat. No. 7,807,186.

(60) Provisional application No. 60/880,826, filed on Jan. 17, 2007.

(51) Int. Cl.
| | |
|---|---|
| *A61K 39/00* | (2006.01) |
| *C12N 5/0783* | (2010.01) |
| *C12N 5/09* | (2010.01) |
| *C12N 15/00* | (2006.01) |
| *C12N 15/867* | (2006.01) |
| *C12N 15/87* | (2006.01) |

(52) U.S. Cl.
USPC .................... 424/93.21; 424/93.7; 424/93.71; 435/325; 435/455; 435/456; 435/465

(58) Field of Classification Search
None
See application file for complete search history.

(56) References Cited

U.S. PATENT DOCUMENTS

| | | | |
|---|---|---|---|
| 5,858,776 A | 1/1999 | Ostrand-Rosenberg et al. | |
| 6,149,905 A | 11/2000 | Ostrand-Rosenberg et al. | |
| 6,319,709 B1 | 11/2001 | Ostrand-Rosenberg et al. | |
| 2002/0018767 A1* | 2/2002 | Lee et al. ................... | 424/93.21 |
| 2002/0086421 A1 | 7/2002 | Ostrand-Rosenberg et al. | |
| 2003/0124103 A1 | 7/2003 | Ostrand-Rosenberg et al. | |
| 2006/0099195 A1 | 5/2006 | Ostrand-Rosenberg et al. | |

OTHER PUBLICATIONS

Albert DM, Niffenegger AS, Willson JK. Treatment of metastatic uveal melanoma: review and recommendations. *Surv Ophthalmol* 1992;36:429-38.
Harbour J. Clinical overview of uveal melanoma: introduction to tumors of the eye. In: Albert DM, Polans A, editors. *Ocular Oncology*. Marcel Dekker; 2003.
Staveley-O'Carroll K, Sotomayor E, Montgomery J, et al. Induction of antigen-specific T cell anergy: an early event in the course of tumor progression. *Proc Natl Acad Sci U S A* 1998;95:1178-83.
Niederkorn JY. See no evil, hear no evil, do no evil: the lessons of immune privilege. *Nat Immunol* 2006;7:354-9.
Streilein JW. Ocular immune privilege: therapeutic opportunities from an experiment of nature. *Nat Rev Immunol* 2003;3:879-89.
Wang JC, Livingstone AM. Cutting edge: CD4+ T cell help can be essential for primary CD8+ T cell responses in vivo. *J Immunol* 2003;171:6339-43.
Kern DE, Klarnet JP, Jensen MC, Greenberg PD. Requirement for recognition of class II molecules and processed tumor antigen for optimal generation of syngeneic tumor-specific class I-restricted CTL. *J Immunol* 1986;136:4303-10.
Ossendorp F, Mengede E, Camps M, Filius R, Melief CJ. Specific T helper cell requirement for optimal induction of cytotoxic T lymphocytes against major histocompatibility complex class II negative tumors. *J Exp Med* 1998;187:693-702.
Ostrand-Rosenberg S, Thakur A, Clements V. Rejection of mouse sarcoma cells after transfection of MHC class II genes. *J Immunol* 1990;144:4068-71.
Bennett SR, Carbone FR, Karamalis F, Miller JF, Heath WR. Induction of a CD8+ cytotoxic T lymphocyte response by cross-priming requires cognate CD4+ T cell help. *J Exp Med* 1997;186:65-70.
Keene JA, Forman J. Helper activity is required for the in vivo generation of cytotoxic T lymphocytes. *J Exp Med* 1982;155:768-82.
Bennett SR, Carbone FR, Karamalis F, Flavell RA, Miller JF, Heath WR. Help for cytotoxic-T-cell responses is mediated by CD40 signalling. *Nature* 1998;393:478-80.
Ridge JP, Di Rosa F, Matzinger P. A conditioned dendritic cell can be a temporal bridge between a CD4+ T-helper and a T-killer cell. *Nature* 1998;393:474-8.
Schoenberger SP, Toes RE, van der Voort EI, Offringa R, Melief CJ. T-cell help for cytotoxic T lymphocytes is mediated by CD40-40L interactions. *Nature* 1998;393:480-3.
Shedlock DJ, Shen H. Requirement for CD4 T cell help in generating functional CD8 T cell memory. *Science* 2003;300:337-9.
Janssen EM, Lemmens EE, Wolfe T, Christen U, von Herrath MG, Schoenberger SP. CD4+ T cells are required for secondary expansion and memory in CD8+ T lymphocytes. *Nature* 2003;421:852-6.
Grakoui A, Shoukry NH, Woollard DJ, et al. HCV persistence and immune evasion in the absence of memory T cell help. *Science* 2003;302:659-62.
Sun JC, Bevan MJ. Defective CD8 T cell memory following acute infection without CD4 T cell help. *Science* 2003;300:339-42.
Mooy CM, De Jong PT. Prognostic parameters in uveal melanoma: a review. *Surv Ophthalmol* 1996;41:215-28.
Peters S, Voelter V, Zografos L, et al. Intra-arterial hepatic fotemustine for the treatment of liver metastases from uveal melanoma: experience in 101 patients. *Ann Oncol* 2006;17:578-83.

(Continued)

*Primary Examiner* — Karen Canella
(74) *Attorney, Agent, or Firm* — Marianne Fuierer; Moore & Van Allen, PLLC

(57) ABSTRACT

The present invention relates to tumor cell-based vaccines and methods of using same, wherein the vaccines are based on naturally immune privileged tumor cells that have been genetically modified to express MHC-II restricted peptides derived from endogenously encoded tumor antigens, activate CD4+ T-lymphocytes, provide an array of antigens to which the host is not tolerized and/or induce immunity against the originating tumor cells as well as against metastatic tumor cells.

14 Claims, 14 Drawing Sheets

OTHER PUBLICATIONS

Noter SL, Rothbarth J, Pijl ME, et al. Isolated hepatic perfusion with high-dose melphalan for the treatment of uveal melanoma metastases confined to the liver. *Melanoma Res* 2004;14:67-72.

Onken MD, Worley LA, Ehlers JP, Harbour JW. Gene expression profiling in uveal melanoma reveals two molecular classes and predicts metastatic death. *Cancer Res* 2004;64:7205-9.

Tschentscher F, Husing J, Holter T, et al. Tumor classification based on gene expression profiling shows that uveal melanomas with and without monosomy 3 represent two distinct entities. *Cancer Res* 2003;63:2578-84.

Svane IM, Engel AM, Nielsen MB, Ljunggren HG, Rygaard J, Werdelin O. Chemically induced sarcomas from nude mice are more immunogenic than similar sarcomas from congenic normal mice. *Eur J Immunol* 1996;26:1844-50.

Shankaran V, Ikeda H, Bruce AT, et al. IFNγ and lymphocytes prevent primary tumour development and shape tumour immunogenicity. *Nature* 2001;410:1107-11.

Danna EA, Sinha P, Gilbert M, Clements VK, Pulaski BA, Ostrand-Rosenberg S. Surgical removal of primary tumor reverses tumor-induced immunosuppression despite the presence of metastatic disease. *Cancer Res* 2004;64:2205-11.

Maat W, Haasnoot GW, Class FH, Schalij-Delfos NE, Schreuder GM, Jager MJ. HLA Class I and II genotype in uveal melanoma: relation to occurrence and prognosis. *Invest Ophthalmol Vis Sci* 2006;47:3-6.

Kan-Mitchell J, Liggett PE, Harel W, et al. Lymphocytes cytotoxic to uveal and skin melanoma cells from peripheral blood of ocular melanoma patients. *Cancer Immunol Immunother* 1991;33:333-40.

van Dinten LC, Pul N, van Nieuwpoort AF, Out CJ, Jager MJ, van den Elsen PJ. Uveal and cutaneous melanoma: shared expression characteristics of melanoma-associated antigens. *Invest Ophthalmol Vis Sci* 2005;46:24-30.

Nabel GJ, Gordon D, Bishop DK, et al Immune response in human melanoma after transfer of an allogeneic class I major histocompatibility complex gene with DNA-liposome complexes. *Proc Natl Acad Sci U S A* 1996;93:15388-93.

Chen PW, Murray TG, Salgaller ML, Ksander BR. Expression of MAGE genes in ocular melanoma cell lines. *J Immunother* 1997;20:265-75.

Radosevich M, Jager M, Ono SJ. Inhibition of MHC class II gene expression in uveal melanoma cells is due to methylation of the CIITA gene or an upstream activator. *Exp Mol Pathol* 2007;82:68-76.

Chang CH, Flavell RA. Class II transactivator regulates the expression of multiple genes involved in antigen presentation. *J Exp Med* 1995;181:765-7.

Sotiriadou R, Perez SA, Gritzapis AD, et al. Peptide HER2(776-788) represents a naturally processed broad MHC class II-restricted T cell epitope. *Br J Cancer* 2001;85:1527-34.

Salazar LG, Fikes J, Southwood S, et al. Immunization of cancer patients with Her-2/neu-derived peptides demonstrating high-affinity binding to multiple class II alleles. *Clin Cancer Res* 2003;9:5559-65.

Thompson JA, Dissanayake SK, Ksander BR, Knutson KL, Disis ML, Ostrand-Rosenberg S. Tumor cells transduced with the MHC class II transactivator and CD80 activate tumor-specific CD4+ T cells whether or not they are silenced for invariant chain. *Cancer Res* 2006;66:1147-54.

Dissanayake SK, Thompson JA, Bosch JJ, et al. Activation of tumor-specific CD4(+) T lymphocytes by major histocompatibility complex class II tumor cell vaccines: a novel cell-based immunotherapy. *Cancer Res* 2004;64:1867-74.

Verbik DJ, Murray TG, Tran JM, Ksander BR. Melanomas that develop within the eye inhibit lymphocyte proliferation. *Int J Cancer* 1997;73:470-8.

Pulaski BA, Ostrand-Rosenberg S. Reduction of established spontaneous mammary carcinoma metastases following immunotherapy with major histocompatibility complex class II and B7.1 cell-based tumor vaccines. *Cancer Res* 1998;58:1486-93.

Baskar S, Glimcher L, Nabavi N, Jones RT, Ostrand-Rosenberg S. Major histocompatibility complex class II+B7-1+ tumor cells are potent vaccines for stimulating tumor rejection in tumor-bearing mice. *J Exp Med* 1995;181:619-29.

Muntasell A, Carrascal M, Alvarez I, et al. Dissection of the HLA-DR4 peptide repertoire in endocrine epithelial cells: strong influence of invariant chain and HLA-DM expression on the nature of ligands. *J Immunol* 2004;173:1085-93.

Dolan BP, Gibbs KD, Jr., Ostrand-Rosenberg S. Tumor-specific CD4+ T cells are activated by "cross-dressed" dendritic cells presenting peptide-MHC class II complexes acquired from cell-based cancer vaccines. *J Immunol* 2006;176:1447-55.

Qi L, Rojas JM, Ostrand-Rosenberg S. Tumor cells present MHC class II-restricted nuclear and mitochondrial antigens and are the predominant antigen presenting cells in vivo. *J Immunol* 2000;165:5451-61.

Armstrong TD, Clements VK, Ostrand-Rosenberg S. MHC class II-transfected tumor cells directly present antigen to tumor-specific CD4+ T lymphocytes. *J Immunol* 1998;160:661-6.

Armstrong TD, Clements VK, Martin BK, Ting JP, Ostrand-Rosenberg S. Major histocompatibility complex class II-transfected tumor cells present endogenous antigen and are potent inducers of tumor-specific immunity. *Proc Natl Acad Sci U S A* 1997;94:6886-91.

Ostrand-Rosenberg S, Pulaski BA, Clements VK, Qi L, Pipeling MR, Hanyok LA. Cell-based vaccines for the stimulation of immunity to metastatic cancers. *Immunol Rev* 1999;170:101-14.

Qin Z, Blankenstein T. CD4+ T cell-mediated tumor rejection involves inhibition of angiogenesis that is dependent on IFN γreceptor expression by nonhematopoietic cells. *Immunity* 2000;12:677-86.

Kujala E, Makitie T, Kivela T. Very long-term prognosis of patients with malignant uveal melanoma. *Invest Ophthalmol Vis Sci* 2003;44:4651-9.

Ganss R, Arnold B, Hammerling GJ. Mini-review: overcoming tumor-intrinsic resistance to immune effector function. *Eur J Immunol* 2004;34:2635-41.

Huang XQ, Mitchell MS, Liggett PE, Murphree AL, Kan-Mitchell J. Non-fastidious, melanoma-specific CD8+ cytotoxic T lymphocytes from choroidal melanoma patients. *Cancer Immunol Immunother* 1994;38:399-405.

Ostrand-Rosenberg, Suzanne. CD4+ T Lymphocytes: A Critical Component of Antitumor Immunity. *Cancer Investigation*, 2005, 23:413-419.

Chen et al. (Experimental Eye Research, Apr. 2006).

Leach et al. (Journal of Immunology, 1995, vol. 154, pp. 738-743).

Abstract of Chen et al. (Invest Opthalmol Vis Sci, 2003, vol. 44, E-abstract 765).

Abstract of Wheeler, Salud d'publica de M'exico, Jul.-Aug. 1997, 39(4):283-287).

Stedman's Medical Dictionary, 27th Edition, 200, Definition for "Vaccine".

Efferson (Anticancer Research, 2005, vol. 25, pp. 715-724).

Bachmann et al. (Journal of Immunology, 2005, vol. 175, pp. 4677-4685).

Streilein et al. (Journal of Immunology, 1997, vol. 158, pp. 3557-3560).

Roitt et al., Ed.s, "Immunology" (textbook), 5th Edition, pp. 91-92 and 141.

Ksander and Streinlein (Chemical Immunology, 1994, vol. 58, pp. 117-145).

\* cited by examiner

A

| Cell Line or PBMC Donor | | HLA Haplotype | | |
|---|---|---|---|---|
| Name | Description | A | B | DR |
| MEL202* | Primary uveal melanoma cell line from patient 202 | 1,3 | 38,52 | 13,15 |
| MEL270*,† | Primary uveal melanoma cell line from patient 270 | 11,29 | 7,52 | 13,15 |
| OMM2.3*,† | Metastatic uveal melanoma cell line from patient 270 | 11,29 | 7,52 | 13,15 |
| H358* | Lung adenocarcinoma cell line | 3 | 35 | 1 |
| SUM159PT* | Mammary adenocarcinoma cell line | 2,24 | 5,15 | 4,13 |
| 308 | Primary uveal melanoma patient | 2,24 | 4,44 | 1,13 |
| M-185 | Metastatic (liver) uveal melanoma patient | 33 | 14,35 | 1,11 |
| Donor 1 | Healthy PBMC donor | 2,74 | 57,72 | 1,11 |
| Donor 2 | Healthy PBMC donor | 74 | 18,72 | 1,13 |
| Donor 3 | Healthy PBMC donor | 2,33 | 15,35 | 1,10 |

* Non-transduced tumor cells constitutively express MHC I and do not express MHC II.

† MEL270 and OMM2.3 tumor cells do not express HLA-B alleles.

Figure 1A

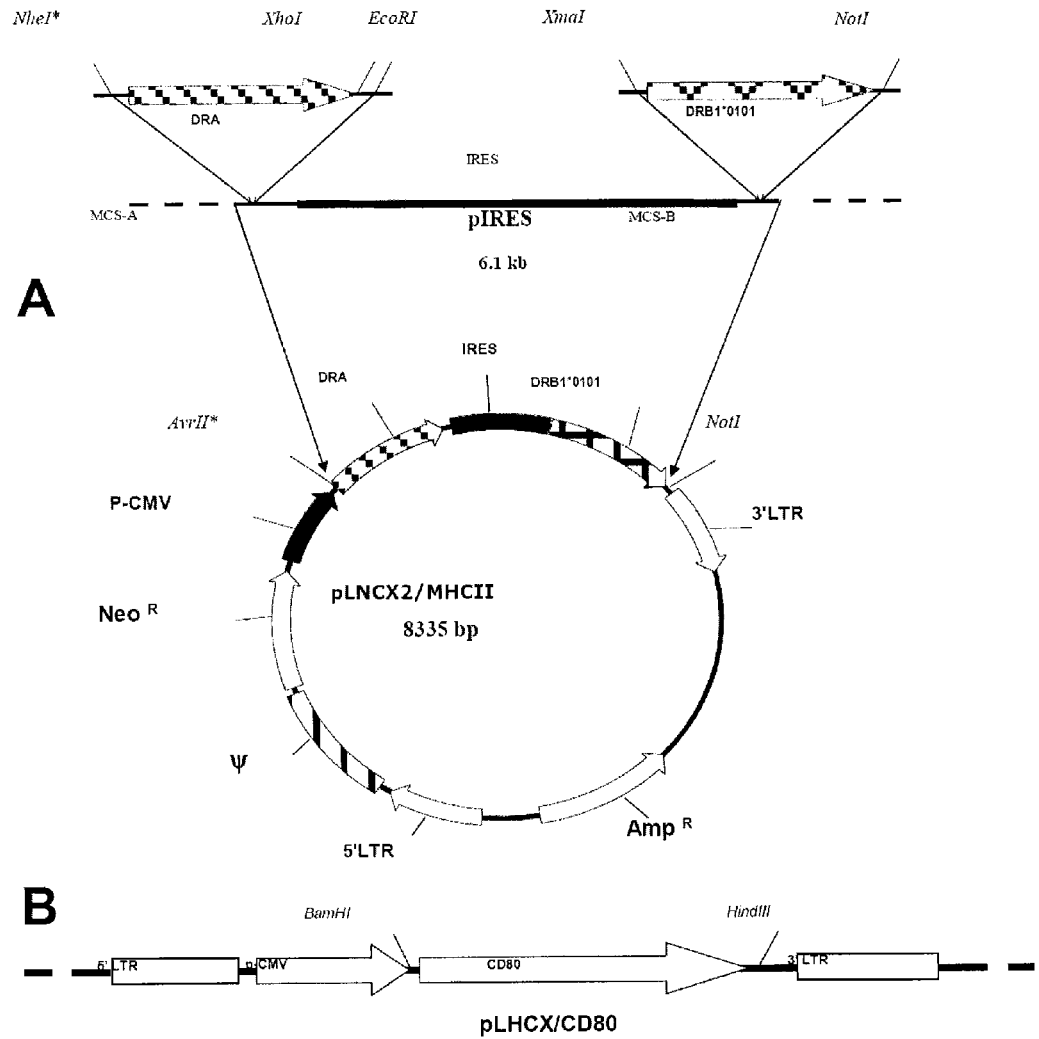
Figures 7A and B

| A | B | C | D | DR | DQ | DP |
|---|---|---|---|---|---|---|
| A1 | B5 |  | Dw1 | DR1 | DQ1 | DPw1 |
| A2 | B7 | Cw2 | Dw2 | DR103 | DQ2 | DPw2 |
| A203 | B703 | Cw3 | Dw3 | DR2 | DQ3 | DPw3 |
| A210 | B8 | Cw4 | Dw4 | DR3 | DQ4 | DPw4 |
| A3 | B12 | Cw5 | Dw5 | DR4 | DQ5(1) | DPw5 |
| A9 | B13 | Cw6 | Dw6 | DR5 | DQ6(1) | DPw6 |
| A10 | B14 | Cw7 | Dw7 | DR6 | DQ7(3) |  |
| A11 | B15 | Cw8 | Dw8 | DR7 | DQ8(3) |  |
| A19 | B16 | Cw9(w3) | Dw9 | DR8 | DQ9(3) |  |
| A23(9) | B17 | Cw10(w3) | Dw10 | DR9 |  |  |
| A24(9) | B18 |  | Dw11(w7) | DR10 |  |  |
| A2403 | B21 |  | Dw12 | DR11(5) |  |  |
| A25(10) | B22 |  | Dw13 | DR12(5) |  |  |
| A26(10) | B27 |  | Dw14 | DR13(6) |  |  |
| A28 | B2708 |  | Dw15 | DR14(6) |  |  |
| A29(19) | B35 |  | Dw16 | DR1403 |  |  |
| A30(19) | B37 |  | Dw17(w7) | DR1404 |  |  |
| A31(19) | B38(16) |  | Dw18(w6) | DR15(2) |  |  |
| A32(19) | B39(16) |  | Dw19(w6) | DR16(2) |  |  |
| A33(19) | B3901 |  | Dw20 | DR17(3) |  |  |
| A34(10) | B3902 |  | Dw21 | DR18(3) |  |  |
| A36 | B40 |  | Dw22 |  |  |  |
| A43 | B4005 |  | Dw23 | DR51 |  |  |
| A66(10) | B41 |  | Dw24 | DR52 |  |  |
| A68(28) | B42 |  | Dw25 | DR53 |  |  |
| A69(28) | B44(12) |  | Dw26 |  |  |  |
| A74(19) | B45(12) |  |  |  |  |  |
| A80 | B46 |  |  |  |  |  |
|  | B47 |  |  |  |  |  |
|  | B48 |  |  |  |  |  |
|  | B49(21) |  |  |  |  |  |
|  | B50(21) |  |  |  |  |  |
|  | B51(5) |  |  |  |  |  |
|  | B5102 |  |  |  |  |  |
|  | B5103 |  |  |  |  |  |
|  | B52(5) |  |  |  |  |  |

Figure 8A

| A | B | C | D | DR | DQ | DP |
|---|---|---|---|----|----|----|
|   | B53 |   |   |   |   |   |
|   | B54(22) |   |   |   |   |   |
|   | B55(22) |   |   |   |   |   |
|   | B56(22) |   |   |   |   |   |
|   | B57(17) |   |   |   |   |   |
|   | B58(17) |   |   |   |   |   |
|   | B59 |   |   |   |   |   |
|   | B60(40) |   |   |   |   |   |
|   | B61(40) |   |   |   |   |   |
|   | B62(15) |   |   |   |   |   |
|   | B63(15) |   |   |   |   |   |
|   | B64(14) |   |   |   |   |   |
|   | B65(14) |   |   |   |   |   |
|   | B67 |   |   |   |   |   |
|   | B70 |   |   |   |   |   |
|   | B71(70) |   |   |   |   |   |
|   | B72(70) |   |   |   |   |   |
|   | B73 |   |   |   |   |   |
|   | B75(15) |   |   |   |   |   |
|   | B76(15) |   |   |   |   |   |
|   | B77(15) |   |   |   |   |   |
|   | B78 |   |   |   |   |   |
|   | B81 |   |   |   |   |   |
|   | B82 |   |   |   |   |   |
|   | Bw4 |   |   |   |   |   |
|   | Bw6 |   |   |   |   |   |

Figure 8B

TUMOR CELLS FROM IMMUNE PRIVILEGED SITES AS BASE CELLS FOR CELL-BASED CANCER VACCINES

CROSS REFERENCE TO RELATED APPLICATIONS

The application is a continuation application of U.S. patent application Ser. No. 12/015,116 filed on Jan. 16, 2008, now U.S. Pat. No. 7,807,186, which in turn claims priority to U.S. Provisional Patent Application No. 60/880,826 filed on Jan. 17, 2007, the contents of which are hereby incorporated by reference herein.

STATEMENT OF GOVERNMENT RIGHTS

This work was supported by grants from the National Institute of Health under contract numbers R01 CA52527, R01 CA84232, R01CA115880, and R01 EY016486. The United States Government has rights to this invention.

BACKGROUND OF THE INVENTION

1. Technology Field

The present invention relates to cell-based vaccines, and more particularly, to vaccines and methods of using same, wherein the vaccines are based on tumor cells from immune-privileged sites that have the ability to activate immunity against the originating tumor cells as well as against metastatic tumor cells.

2. Related Art

Immunotherapy is a potential approach for the treatment and/or prevention of cancer because of its specificity, sensitivity, potency, and long-term memory. Induction of a T lymphocyte response is a critical initial step in a host's immune response. Activation of T cells results in T cell proliferation, cytokine production by T cells and generation of T cell-mediated effector functions. T cell activation requires an antigen-specific signal, often called a primary activation signal, which results from stimulation of a clonally-distributed T cell receptor (hereafter TcR) present on the surface of the T cell. This antigen-specific signal is usually in the form of an antigenic peptide bound either to a major histocompatibility complex (hereafter MHC) class I protein or an MHC class II protein present on the surface of an antigen presenting cell (hereafter APC). CD4+ T cells recognize peptides associated with class II molecules. Class II molecules are found on a limited number of cell types, primarily B cells, monocytes/macrophages and dendritic cells, and, in most cases, present peptides derived from proteins taken up from the extracellular environment. In contrast, CD8+ T cells recognize peptides associated with class I molecules. Class I molecules are found on almost all cell types and, in most cases, present peptides derived from endogenously synthesized proteins.

Notably, CD4+ T lymphocytes long have been recognized by tumor immunologists as critical elements for priming tumor-specific CD8+ T cells. They also are required for effective immunity during chronic infections, a scenario similar to prolonged tumor growth and progression. T cells that are cytotoxic for tumor cells are typically CD8+ T lymphocytes, and optimal activation of these cells usually requires coactivation of CD4+ T helper lymphocytes. CD4+ T lymphocytes are also required for generating CD8+ T memory cells.

Primary ocular or uveal melanoma is the most common malignancy of the eye and can be effectively treated with a variety of therapies, such as plaque radiotherapy, laser photocoagulation, transpupillary thermotherapy, trans-scleral resection, or enucleation of the tumor-bearing eye. Although these treatments limit the growth of the primary tumor and may partially preserve vision, they do not prevent the development of metastases, which occurs in ~50% of patients with large tumors (1-3) and is universally fatal within ~4 to 9 months of diagnosis (4). Although several treatments are available that increase median survival time to ~15 months, metastatic uveal melanoma remains universally fatal (5,6).

Thus it would be advantageous to develop cell-based tumor vaccines that are effective at activating both CD4+ and CD8+ T lymphocytes to induce antitumor immunity in patients with tumor producing diseases and also provide immunity that is cross-reactive with other types of metastatic tumors.

SUMMARY OF THE INVENTION

The present invention relates to cell based vaccines comprising primary tumor cells from immune-privileged sites or tissue to provide vaccines that activate CD4+ T-lymphocytes, present MHC-II restricted peptides derived from endogenously encoded tumor antigens and/or provide an array of antigens to which the host is not tolerized. The immune privileged sites or tissues, may include, but are not limited to, the eye (anterior chamber, cornea and retina); brain; cartilages; liver; adrenal cortex; uterus and placenta; ovary and testis; prostate and tumor cells.

In one aspect, the present invention provides for genetically modified naturally immune privileged tumor cells that express MHC-II restricted peptides derived from endogenously encoded tumor antigens and a co-stimulatory molecule. The immune-privileged tumor cells may be derived from immune privileged sites or tissues, including the eye; brain; cartilages; liver; adrenal cortex; uterus and placenta; ovary and testis; prostate and tumor cells. For example, the immune-privileged tumor cells may be derived from one of the tissues of the eye including the iris, ciliary body, retina, and corneal endothelium, and preferably from primary uveal melanoma cells.

In another aspect, the present invention provides a tumor cell-based vaccine for a recipient comprising:
  a primary immune-privilege tumor cell that constitutively express MHC class I molecules and does not constitutively express MHC class II molecules; and is genetically modified to express a co-stimulatory molecule that activates T-cells and at least one MHC class II allele, wherein the MHC class II allele is syngeneic to the recipient.

Another aspect, the present invention provides a tumor cell-based vaccine for a recipient comprising:
  a primary uveal melanoma cell that constitutively express MHC class I molecules and does not constitutively express MHC class II molecules and is genetically modified to express a co-stimulatory CD80 molecule and at least one MHC class II allele, wherein the MHC class II allele is syngeneic to the recipient.

In yet another aspect, the present invention provides for a MHC II-matched allogeneic cell-based vaccine comprising:
  primary immune-privilege tumor cells that constitutively express MHC class I molecules and do not constitutively express MHC class II molecules, wherein the primary immune-privilege tumor cells do not constitutively express accessory molecules including Ii; and wherein the primary immune-privilege tumor cells are genetically modified to express co-stimulatory molecules that activate T-cells and MHC class II alleles.

In a still further aspect, the present invention provides for a method to prime and boost IFNγ-secreting CD4+ cells from PBMC, the method comprising;

administering to a subject a therapeutically effective amount of a tumor cell-based vaccine comprising:
   a primary tumor cell that constitutively express MHC class I molecules and does not constitutively express MHC class II molecules and Ii; and
   is genetically modified to express a co-stimulatory molecule that activates CD4+ T cells, and at least one MHC class II allele, wherein the MHC class II allele is syngeneic to the subject.

Another aspect of the present invention provides for a method of generating a MHC-II matched allogeneic cell based vaccine that cross reacts with multiple patients and treat metastatic tumors, the method comprising:
  a. providing primary immune-privilege tumor cells;
  b. determining the HLA type of the primary immune-privilege tumor cells
  c. isolating primary immune-privilege tumor cells that cannot be induced to express MHC II or Ii;
  d. transducing the isolated primary immune-privilege tumor cells with at least one vector comprising nucleotide sequences encoding for the determined HLA-D allele or a variant thereof, wherein the HLA-D allele is selected from HLA-DR, HLA-DQ and HLA-DP, and a co stimulatory molecule that activates CD4+ T cells or variant thereof to provide tumor cells that express the transduced HLA-DR and co stimulatory molecules.

Yet another aspect of the present invention provide for a method of generating a MHC-II matched allogeneic tumor cell based vaccine that cross reacts with multiple patients and treat metastatic tumors, the method comprising:
  a. providing primary uveal melanoma cells that arise from ocular immune-privileged tissue;
  b. determining the HLA type of the primary uveal melanoma cells;
  c. isolating primary uveal melanoma cells that cannot be induced to express MHC II or Ii;
  d. transducing the isolated primary uveal melanoma cells with at least one vector comprising nucleotide sequences encoding for the determined HLA-DR allele or a variant thereof and a co stimulatory molecule or variant thereof to provide cells that express the transduced HLA-DR and co stimulatory molecules.

A still further aspect of the present invention provides for a method of converting immune-privilege tumor cells into antigen presenting cells, the method comprising:
  providing immune-privilege tumor that do not express Ii or MHC II protein and transducing same with a MHC II allele (HLA-DR, HLA-DQ or HLA-DP) syngeneic to a recipient and a costimulatory molecule, wherein the modified immune-privilege tumor cells activate CD4+ T-cells. Optionally, if the transduced immune-privilege tumor cells are MHC I (HLA-A, B or C) matched to the recipient, the modified uveal melanoma cells will also activate CD8+ T cells.

In yet another aspect, the present invention provides for an immunovaccine composition for administering to a subject in need of treatment for primary and/or metastatic cancers, the vaccine comprising at least two multiple immune-privilege tumor cell lines that include at least two different MHC II alleles of the subject being treated.

In a further aspect, the present invention provides for an immunovaccine composition for administering to a subject in need of treatment for primary and/or metastatic uveal melanoma, the vaccine comprising at least two multiple uveal melanoma cell lines that include at least two different MHC II alleles of the subject being treated.

Another aspect of the present invention provides a method of enhancing and/or potentiating an immune response in a subject, comprising: directly administering to the subject a polynucleotide comprising nucleic acid sequences encoding CD80 and HLA-DR, operably linked to a promoter sequence that controls the expression of said nucleic acid sequence, said polynucleotide being present in an amount sufficient that uptake of said polynucleotide into one or more primary immune-privilege tumor cells that does not express a MHC II or Ii of the subject occurs and sufficient expression of said nucleic acid sequence results in the production of a polypeptide effective to enhance or modify an immune response.

In another aspect, the cell based tumor vaccines may be used to identify MHC class II-restricted peptide epitopes that are recognized by CD4+ T cells. Once the epitopes are determined the identified peptides may be analyzed, such as in a murine model system, for their ability to activate CD4+ T cells, and whether the resulting activated CD4+ T cells can enhance CD8+ T cell responses against a tumor.

A still further aspect provides for an ex vivo method for inducing an increased population of CD4$^+$ T cells in a subject, comprising:
  (a) removing a blood sample from the subject and isolating CD4+ and/or CD8+ T-cells therefrom;
  (b) determining HLA genotypes of the subject;
  (c) contacting the CD 4+ and or CD8+ T-cells with a vaccine comprising:
    a primary immune-privilege tumor cell that constitutively express MHC class I molecules and does not constitutively express MHC class II molecules and Ii; and
    is genetically modified to express a co-stimulatory molecule that activates CD4+ T-cells and at least one MHC class II allele, wherein the MHC class II allele is syngeneic to the HLA genotype of the subject; and
  (d) reintroducing the activated CD4+ and or CD8+ T-cells into the subject.

Other aspects and advantages of the invention will be more fully apparent from the ensuing disclosure and appended claims.

BRIEF DESCRIPTION OF THE FIGURES

FIGS. 7A and B show the retroviral constructs made and used in these studies. A, the pLNCX2/MHC II construct contains the DRA and DRB0101 cDNAs flanking an IRES and under the control of the cytomegalovirus (CMV) promoter and contains the G418 resistance gene. B the pLHCX/CD80 construct that encode the human CD80 gene and contain the hygromycin resistance gene.

FIGS. 8A and B show some recognized serological and cellular HLA specificities.

DETAILED DESCRIPTION OF THE INVENTION

Definitions

Figures 1B, 1C:
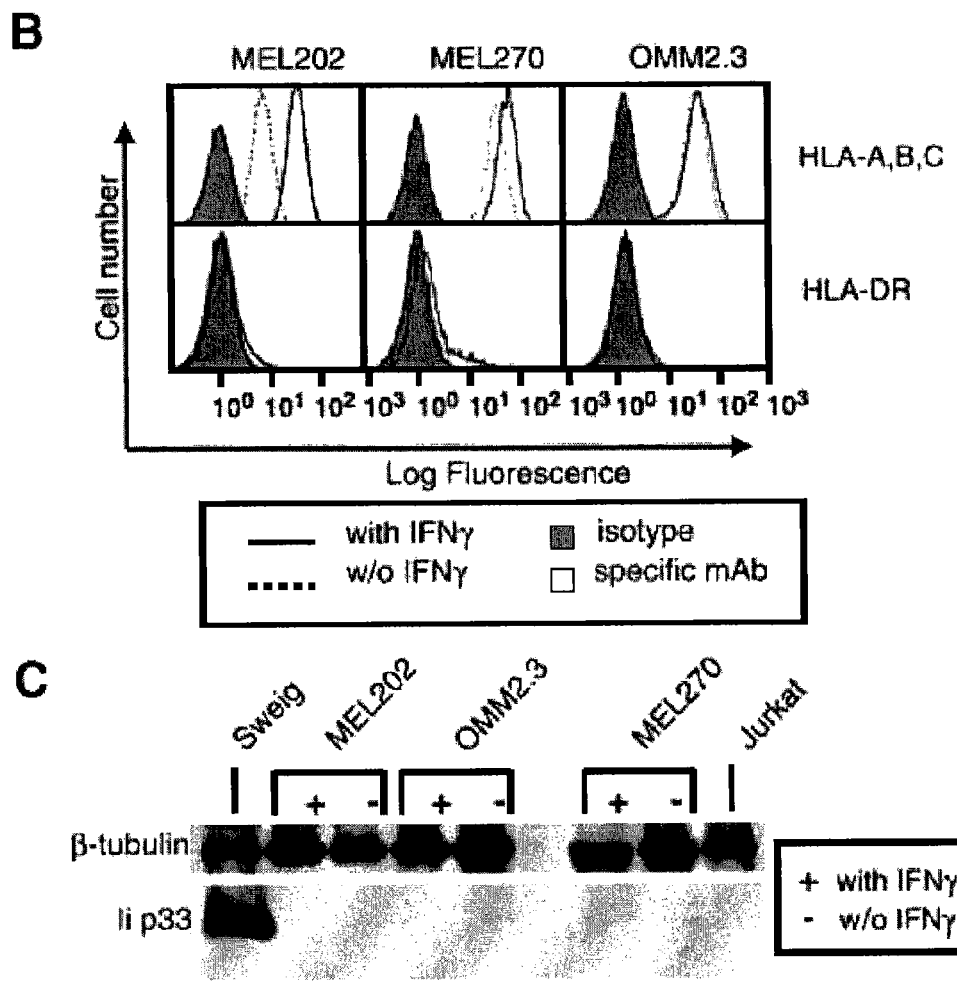
FIGS. 1A, B and C show that primary (MEL202 and MEL270) and metastatic (OMM2.3) uveal melanomas do not express HLA-DR or Ii, even in the presence of exogenous IFNγ. A, HLA alleles of patient's and healthy donor's PBMC and uveal melanoma, breast, and lung cancer cells used in these studies. B, uninduced (−IFNγ) or IFNγ-treated (+IFNγ) MEL202, MEL270, and OMM2.3 live cells were stained for plasma membrane MHC I (mAb W6/32-PE) or MHC II (mAb L243-PE) and analyzed by flow cytometry. C, uninduced (−) or IFNγ-treated (+) MEL 202, MEL270, and OMM2.3 were detergent lysed, electrophoresed on 10% SDS-PAGE gels under nonreducing conditions, and transferred to nitrocellulose. Blots were stained for Ii (mAb PIN1.1) or B-tubulin (mAb anti-B-tubulin clone 2.1). Sweig and Jurkat cells are Ii+ and Ii− control cells, respectively. These data are representative of two independent experiments.

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response.

The term "antigen presenting cell" (APC) as used herein, is defined as a cell that are capable of activating T cells or other immune cells, and includes, but is not limited to, monocytes/macrophages, B cells and dendritic cells (DCs).

The term "autologous" as used herein is defined as material derived from the same individual to whom it is later to be re-introduced therein.

The term "xenogeneic" as used herein is defined as a material derived from a different animal species than the animal species that becomes the recipient of the vaccine.

The term "allogeneic" as used herein is defined as a material derived from the same animal species but genetically different in one or more genetic loci as the animal that becomes the "recipient." This usually applies to tumor cells transplanted from one animal to another non-identical animal of the same species.

The term "syngeneic" as used herein is defined as a material derived from the same animal species and has the same genetic composition for most genotypic and phenotypic markers as the recipient.

The term "immune-privilege tumor cells" as used herein is defined as tumors including uveal melanomas, retinoblastoma, intraocular lymphoma; brain tumors; prostate tumors; and any other tumors that originate from immune-privilege tissue.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, ocular cancer, pancreatic cancer, colorectal cancer, renal cancer, liver cancer, brain cancer, lymphoma, leukemia, lung cancer and the like.

The term "immune privilege site" as used herein is defined as regions of the body where allogeneic or xenogeneic grafts of foreign tissue enjoy prolonged, even indefinite, survival relative to nonprivileged sites Immune privileged sites and tissues include the eye (anterior chamber, cornea, and retina) brain, hair follicles, cartilage, liver, adrenal cortex, uterus and placenta during pregnancy, ovary and testis, prostate and tumors.

The term "encoding" as used herein is defined as the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "endogenous" as used herein is defined as any material from or produced inside an organism, cell, tissue or system.

The term "exogenous" as used herein is defined as any material introduced from or produced outside an organism, cell, tissue or system.

The term "activation", as used herein is defined as the state of a T cell that has been sufficiently stimulated to induce detectable cytokine production, detectable effector functions and/or cellular proliferation.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

The term "major histocompatibility complex", or "MHC", as used herein is defined as a specific cluster of genes, many of which encode evolutionarily related cell surface proteins involved in antigen presentation, which are among the most important determinants of histocompatibility. Class I MHC, or MHC-I, function mainly in antigen presentation to CD8 T lymphocytes. Class II MHC, or MHC-II, function mainly in antigen presentation to CD4 T lymphocytes. The MHC gene, located on chromosome 6, includes HLA genes divided into distinct regions including Class I genes that encode for a heavy chain polypeptide located in the HLA-A, B and C regions; and Class II genes including the D region which is subdivided in three main regions, DP, DQ and DR, each containing genes for a number of α and β chains. A complete listing of current HLA specificities, any of which may be used in the present immunovaccines, and corresponding sequences, both nucleotide and amino acid, can be located at the IMGT/HLA Database at "http://www.ebi.ac.uk/imgt/hla" which provides a database for sequences of the human major histocompatibility complex (HLA) and includes the official sequences for the WHO Nomenclature Committee For Factors of the HLA System. The IMGT/HLA Database is part of the international ImMunoGeneTics project.

The term "T-cell" as used herein is defined as a thymus-derived cell that participates in a variety of cell-mediated immune reactions. Most of the T cells in the body belong to one of two subsets. These are distinguished by the presence on their surface of one or the other of two glycoproteins designated: CD4 and CD8. Which of these molecules is present determines what types of cells the T cell can bind to. CD8+ T cells bind epitopes that are part of class I histocompatibility molecules. Almost all the cells of the body express class I molecules. CD4+ T cells bind epitopes that are part of class II histocompatibility molecules. The best understood CD8+ T cells are cytotoxic T lymphocytes (CTLs). They secrete molecules that destroy the cell to which they have bound. CD4+ T cells bind an epitope consisting of an antigen fragment lying in the groove of a class II histocompatibility molecule. CD4+ T cells are essential for both the cell-mediated and antibody-mediated branches of the immune system. Activated CD4+ T cells are either Type 1 (Th1) or Type 2 (Th2), or Type 17 (Th17) based on their cytokine secretion profile. Type 1 cells secrete IL-2, IFNγ, TNFα, GM-CSF, and; Th2 cells secrete, IL-4, IL-5, IL-10, and IL-13. Type 1 CD4+ T-cells, which secrete IFNγ, are a critical component for the activation of CD8+ T cells, either through the "helper" T cells that provide cytokine support for CD8+ T cells or by the induction of CD40 on dendritic cells which in turn activate CD8+ T cells. CD4+ T cells are essential for generating CD8+ T memory cells, for preventing CD8+ T cells from being tolerized and for recriting cells of the inname immue system. As previously stated, Type 1 cells provide help to cytotoxic CD8+ T cells, Type 2 cells facilitate antibody production by B lymphocytes, whileType 3 cells produce IL-17. It is believed that immune responses skewed toward CD4+ Type 1 cells and away from Type 2 responses are optimal for antitumor immunity because CD8-mediated killing is highly efficient for destroying tumor cells. Further, Type 1 cytokine IFNγ plays an important role in regulating in vivo tumor growth by both the innate and adaptive immune systems. IFNγ is a pleiotropic cytokine that has many effects ranging from stimulation of T cell-mediated and NK responses to enhancing MHC class I and class II expression on target cells.

The term "costimulatory" as used herein is defined as a molecule that binds to a receptor on a T cell that is involved in the activation of the T cell In order to become activated, the T cells must not only bind to the epitope (MHC-peptide) with its TCR but also receive a second signal from a costimulator. Among the most important of these costimulators are molecules designated B7, wherein B7 comes in two forms: B7-1 (CD80) and B7-2 (CD86), and their ligand on the T cell designated CD28 and/or CTLA-4. The binding of CD28 to B7 provides the second signal needed to activate the T cell. The present invention includes B7-1 and B7-2 polypeptides and nucleic acids encoding same and also all such polypeptide variants (and nucleic acids encoding such polypeptide variants) that exhibit properties similar or equivalent to the properties of the CD28 binding partners wherein such polypeptide variants have a CD28 binding affinity about equal to, equal to, or greater than the CD28 binding affinity for B7-1 or B7-2 and/or an ability to induce a T-cell proliferation, and/or a T-cell activation response about equal to, equal to, or greater than that of B7-1 or B7-2. Such variants may included the B7-H1/PD-L1 with binding affinity for CTLA-4; B7-H2 with binding affinity for ICOS; B7-H3 with binding affinity for PD-1; B7-H4 with binding affinity for PD-L2) or any other co-stimulatory molecules.

The term "B-cell" as used herein is defined as a cell derived from the bone marrow and/or spleen. B cells can develop into plasma cells which produce antibodies.

The term "therapeutically effective amount" as used herein is defined as an amount of a therapeutic composition sufficient to provide a beneficial effect to a mammal to which the composition is administered which may include no change in the cancer, which can be beneficial inasmuch as the cancer does not get worse, to a reduction in cancer (size of a tumor and/or number of tumor) or an inhibition of metastasis of the cancer. One skilled in the art also is aware of means to monitor a therapeutic (i.e., systemic immune) response upon administering a composition of the present invention. In particular, the therapeutic response can be assessed by monitoring attenuation of tumor growth and/or tumor regression. The attenuation of tumor growth or tumor regression in response to treatment can be monitored using several end-points known to those skilled in the art including, for instance, number of tumors, tumor mass or size, or reduction/prevention of metastasis. The skilled artisan would understand that the effective amount varies and can be readily determined based on a number of factors such as the age and health and physical condition of the mammal being treated, the severity of the disease, the particular cell being administered, the level of activation of T cells, and the like. Generally, the effective amount will be set between about 0.1 mg/kg to about 100 mg/kg, more preferably from about 1 mg/kg and 25 mg/kg.

The term "combination therapy" as used herein is defined as combining the methods and immunovaccines of the present invention with other methods of cancer treatment. Examples of such methods include radiation, surgery and chemotherapy.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "immunovaccine," as used herein is defined as a vaccine that can elicit a detectable immune response when administered to an animal. More preferably, an immunovaccine stimulates and activates T cells when administered to the animal, such that it generates a detectable T cell immune response to a antigen, a tumor cell, and the like, when compared to a T cell the immune response, if any, in an otherwise identical animal to which the immunovaccine is not administered.

The term "variant" as used herein, is defined as a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

The term "vector" as used herein is defined as a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, a lentiviral vector, a recombinant adenovirus, a recombinant retrovirus, a recombinant adeno-associated virus, a recombinant avian pox virus, and the like. Examples of non-viral vectors include, but are not limited to, liposomes, polyamine derivatives of DNA, and the like.

The term "administering" as used herein is defined as the actual physical introduction of the composition into or onto (as appropriate) the host subject. Any and all methods of introducing the composition into the subject are contemplated according to the present invention; the method is not dependent on any particular means of introduction and is not to be so construed. Means of introduction are well-known to those skilled in the art, and preferably, the composition is administered subcutaneously or intratumorally. One skilled in the art will recognize that, although more than one route can be used for administration, a particular route can provide a more immediate and more effective reaction than another route. Local or systemic delivery can be accomplished by administration comprising application or instillation of the immunovaccines into body cavities, inhalation or insufflation of an aerosol, or by parenteral introduction, comprising intramuscular, intravenous, intraportal, intrahepatic, peritoneal, subcutaneous, or intradermal administration. In the event that the tumor is in the central nervous system, the composition must be administered intratumorally because there is no priming of the immune system in the central nervous system.

The immunovaccines of the present invention can be used alone or in appropriate association, as well as in combination, with other pharmaceutically active compounds as are known in the art. For example, In one embodiment, the cell-based tumor vaccines composed of primary tumor cells from immune-privilege tissue have been found effective at inducing antitumor immunity in patients and are cross-reactive with metastatic tumor cells. For example, using the uveal melanomas that arise in the eye, an immune-privileged site, also provides molecules to which the host is not tolerized. The MHC II primary immune-privilege vaccines of the present invention are designed to activate HLA-DR-restricted CD4+ T cells and thereby generate protective tumor immunity and immune memory in cancer patients who are at high risk of developing metastatic disease. Importantly, it has been shown that the present MHC II immune-privilege vaccines efficiently activate tumor-reactive, IFNγ-secreting, MHC II-restricted CD4+ T cells from healthy donors and patients; with cancer tumors, therefore, these data are an important step toward showing the therapeutic efficacy of this approach. The following examples will show the effectiveness of (generalize to other tumors?)

In another embodiment, the present invention includes cell-based vaccines that activate tumor-specific CD4+ T cells, comprising, consisting essentially of or consisting of tumor cells that constitutively express MHC class I (MHC I) molecules, do not constitutively express MHC class II (MHC II) molecules, and are genetically modified to express CD80 costimulatory molecules and MHC II alleles that are syngeneic to the recipient. Because the MHC II-matched allogeneic "MHC II vaccine" cells do not constitutively express the MHC II accessory molecule, Ii, they preferentially present endogenously synthesized tumor peptides rather than exogenously derived peptides (25). Expression of both CD80 and MHC II allows the vaccine to directly present antigens that prime MHC II-matched naive T cells (26-28). Recent studies indicate that tumor cell vaccines also activate CD4+ T cells through the process of cross-dressing, in which the MHC II-peptide complexes are transferred from the vaccine cells onto the surface of host dendritic cells (29). Therefore, tumor cell vaccines of the present invention possess both a direct and indirect route of activating tumor-specific CD4+ T cells.

In yet another embodiment, the present invention includes cell-based tumor vaccines composed of primary uveal melanomas that have been found effective at inducing antitumor immunity in patients and are cross-reactive with metastatic uveal melanoma cells. Importantly, using the uveal melanomas that arise in the eye, an immune-privileged site, also provides molecules to which the host is not tolerized. The MHC II uveal melanoma vaccines of the present invention are designed to activate HLA-DR-restricted CD4+ T cells and thereby generate protective tumor immunity and immune memory in uveal melanoma patients who are at high risk of developing metastatic disease. Importantly, it has been shown that the present MHC II uveal melanoma vaccines efficiently activate tumor-reactive, IFNγ-secreting, MHC II-restricted CD4+ T cells from healthy donors and uveal melanoma patients; therefore, these data are an important step toward showing the therapeutic efficacy of this approach.

Notably, it has been found that the present vaccines, prepared from individual patients' primary uveal melanoma cells, have activated CD4+ T cells that cross-reacted with aggressive primary and metastatic tumor cells derived from other uveal melanoma patients, suggesting that the genetically modified, nonautologous vaccines may be useful reagents for stimulating tumor immunity in uveal melanoma patients.

This cross-reactivity also suggests that a "cocktail vaccine" may be the most effective and feasible approach for adapting the MHC II vaccines for clinical use. Thus, vaccine cocktails of the present invention would consist of a pool of two to eight individual primary immune-privilege tumor cell lines, preferably, four to six cell lines, each transduced with CD80 (or an equivalent costimulatory molecule) and a HLA-D (selected from R, Q or P) allele shared with the recipient. It is likely that some of the cell lines within the cocktail will share tumor antigens with the patient; hence, immunization with the cocktail will induce cross-reactivity with the patient's tumor. By maintaining a frozen bank of individual immune-privilege tumor cell lines, each transduced with a common HLA-DR allele and CD80 (or an equivalent costimulatory molecule), a vaccine cocktail could readily be customized for an individual patient. For example, for a HLA-DR4+DR7+ patient, four to six immune-privilege tumor cell lines from the bank of DR4+CD80+ and DR7+CD80+ transductants could be pooled.

For example, a bank may include frozen individual uveal melanoma cell lines, each transduced with a common HLA-DR allele and CD80 (or an equivalent co-stimulatory molecule), a vaccine cocktail may be customized for an individual patient. For example, for a HLA-DR4+DR7+ patient, four to six uveal melanoma cell lines from the bank of DR4+CD80+ and DR7+CD80+ transductants can be pooled.

Figure 9:
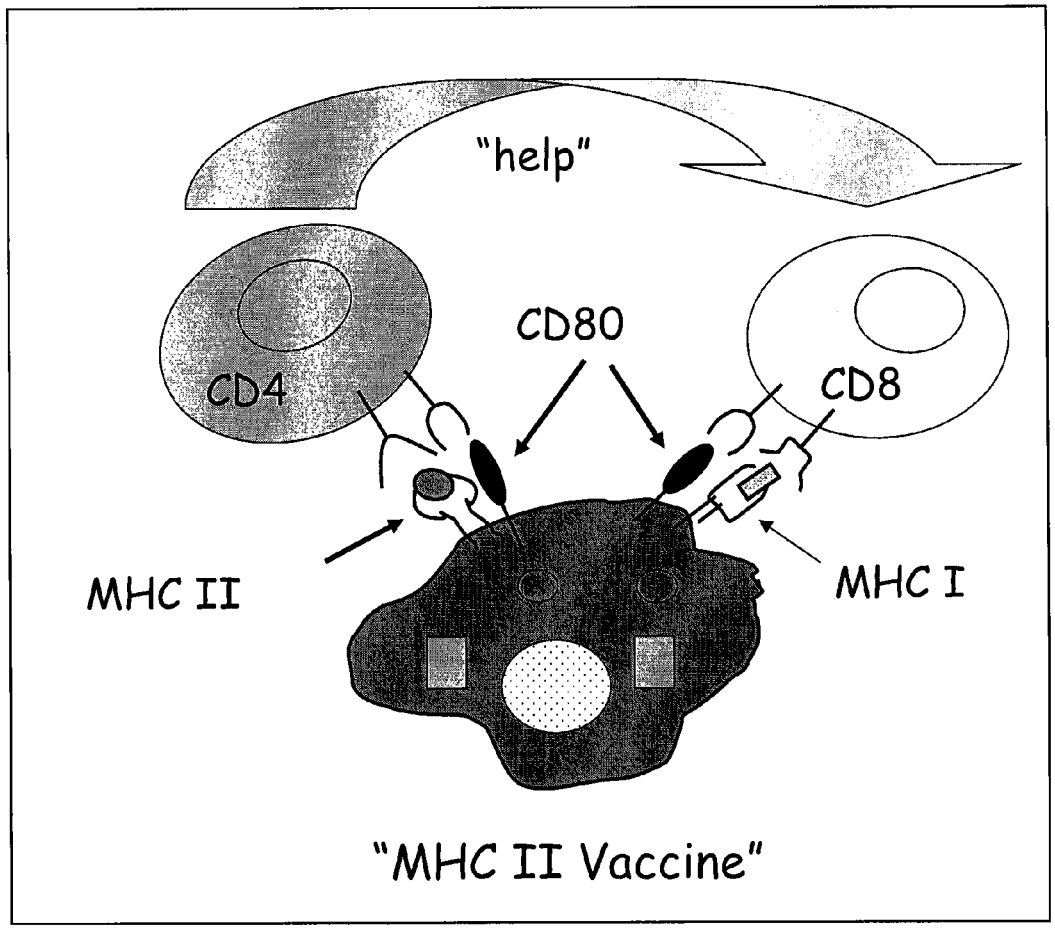
FIG. 9 illustrates the MHC II vaccines of the present invention that are genetically modified tumor cells and also shows the activation of both CD4+ and CD8+ T cells from the same cell.

It is known that CD4+ T cells facilitate tumor immunity by contributing to the activation of CD8+ cytotoxic T cells and enhancing the generation of long-term immune memory. They mediate their effects by interacting with CD8+ T cells and/or dendritic cells (14, 15, 18) and, therefore, once activated, do not need to directly react with tumor cells. Because the MHC II uveal melanoma vaccines described herein coexpress MHC I, MHC II, and costimulatory molecules and thus also activate tumor-reactive CD4+ T cells, it is believed that they will also activate MHC I-restricted, tumor-reactive CD8+ T cells, provided that the vaccine cells share at least one MHC I allele with the recipient. MHC I matching will be feasible for at least 50% of patients because the HLA-A2 allele is expressed by ~50% of uveal melanoma patients (44). Thus, CD4+ and CD8+ T cells are activated on the same vaccine cell so help for activation of CD8+ is local as shown in FIG. 9.

Due to HLA polymorphism, a cocktail vaccine of the present invention is likely to be partially MHC I allogeneic to the recipient. However, allo-MHC I differences neither adversely affect nor dominate the generation of tumor-specific CD4+ T cells because it has been found that alloreactivity may be beneficial and have an adjuvant effect.

Notably, the present immunovaccines may be appropriate to treat uveal melanoma because of the progression of the disease. Typically, patients with primary uveal melanoma are diagnosed before they develop overt metastasis, and they have a lengthy disease-free interval before metastases become clinically detectable (3, 4). Therefore, once the primary tumor is eliminated, patients have minimal residual disease, reducing the likelihood of immune suppression, which is associated with large, bulky tumor burdens (46). In the absence of tumor-induced immune suppression, patients are more likely to actively respond to vaccination and to produce tumor-reactive CD4+ and CD8+ T cells.

Further, the location of primary tumor in the eye may also be advantageous for immunotherapy against metastatic uveal melanoma. Because the eye is an immune-privileged site, tumor cells residing there may express molecules to which the host is not tolerized (8, 9) and, therefore, be inherently more immunogenic than tumor cells from nonprivileged sites. The results shown herein provide proof that MHC II uveal melanoma vaccines made from primary tumor cells are significantly better activators of CD4+ T cells than vaccines prepared from metastatic cells.

Microarray and cytogenetic studies of primary tumors can be conducted to help identified chromosomal aberrations and genes that may be predictive of progression to metastatic disease. For example, in primary uveal melanomas, the primary tumors exhibiting monosomy of chromosome 3 are believed to be significantly more metastatic than primary tumors with normal chromosome numbers (49). Likewise, primary tumors that express high levels of E-cadherin and β-cadherin in combination with certain epithelial characteristics are thought to metastasize at much higher frequency than primary tumors with low levels of these gene products (50).

If classification of primary tumors is sufficiently prognostic of tumor progression, then the MHC II tumor based cell vaccines of the present invention may not only be useful for the treatment of established metastatic disease but could also be used as prophylactic reagents for the treatment of the 50% of patients with large primary tumors who are identified as being at high risk for developing metastatic disease.

The MHC II vaccines of the present invention have several advantages that favor the activation of tumor-specific CD4+ T cells. For example, transduced MHC II+Ii− cells present additional MHC II-restricted peptides that are not presented by MHC II+Ii+ cells (26-28, 30); therefore, the recipient is exposed to a larger repertoire of peptides than the repertoire presented by professional antigen-presenting cells (APC). Further, if the additional tumor peptides are novel, then the recipients will not previously have been exposed to them and hence will not be tolerized to them. Still further, the vaccine cells synthesize many proteins that are potential tumor antigens; hence, multiple MHC II-restricted tumor peptides will be presented. Also, it is not necessary to identify or characterize tumor antigens because the MHC II-restricted peptides are constitutively processed and presented by the vaccine cells. Further, when the MHC II vaccines coexpress MHC I molecules that are shared with the host, then tumor-specific CD8+ T cells can also be activated.

Surprisingly, it has been found that the MHC II vaccines of the present invention prepared from human primary uveal melanoma cells activate naive CD4+ T cells from either healthy donors or uveal melanoma patients. Further, it has been found that activated T cells produce high levels of IFNγ and cross-react with primary tumors from other patients and metastatic uveal melanoma cells. In contrast, vaccines prepared from metastatic uveal melanoma cells are much less efficient at activating CD4+ T cells, suggesting that tumor cells originating in immune-privileged sites have enhanced capacity for inducing antitumor immunity and for serving as immunotherapeutic agents.

Primary immune-privilege tumor cells can be modified ex vivo to express the HLA-DR and costimulatory molecule by transfection of isolated primary tumor cells that do not express MHC Class II molecules or Ii with nucleic acid sequences encoding the HLA-DR and costimulatory molecules in a form suitable for expression of the molecule on the surface of the tumor cell. Transfection which refers to the introduction of exogenous nucleic acid into a mammalian cell and encompass a variety of techniques useful for introduction of nucleic acids into mammalian cells including electroporation, calcium-phosphate precipitation, DEAE-dextran treatment, lipofection, microinjection and infection with viral vectors. Suitable methods for transfecting mammalian cells can be found in Sambrook et al. (Molecular Cloning: A Laboratory Manual, 2nd Edition, Cold Spring Harbor Laboratory press (1989)) and other laboratory textbooks.

Specifically, uveal melanoma cell tumor cells are transfected with one or more nucleic acids encoding one or more MHC class II α chains and one or more MHC class II β chains in a form suitable for expression of the MHC class II molecules(s) on the surface of the tumor cell. Both an α and a β chain proteins must be present in the tumor cell to form a surface heterodimer and neither chain will be expressed on the cell surface alone.

The nucleic acid sequences of many human class II genes are known. For examples see the IMGT/HLA Database at "http://www.ebi.ac.uk/imgt/hla." MHC class II genes may include genes as set forth in Table 1.

TABLE 1

|  | Alpha | Beta |
|---|---|---|
| HLA-DM | HLA-DMA | HLA-DMB |
| HLA-DO | HLA-DOA | HLA-DOB |
| HLA-DP | HLA-DPA1 | HLA-DPB1 |
| HLA-DQ | HLA-DQA1, HLA-DQA2 | HLA-DQB1, HLA-DQB2, HLA-DQB3 |
| HLA-DR | HLA-DRA | HLA-DRB1, HLA-DRB2, HLA-DRB3, HLA-DRB4, HLA-DRB5 |

Preferably, the α chain is HLA-DRA and the β chain is HLA-DRB1. Further preferably, the introduced MHC class II molecule is a self MHC class II molecule meaning the gene is expressed by the recipient of the vaccine. The immune-privilege tumor cells to be transfected cannot and do not express MHC class II molecules on their surface prior to transfection The nucleic acid to be introduced can be, for example, DNA encompassing the gene encoding the HLA-DR and costimulatory molecules, sense strand RNA encoding the costimulatory molecule or a recombinant expression vector containing a cDNA encoding the HLA-DR and costimulatory molecules. Preferred human cDNAs to use include the nucleotide sequence of the human CD80 cDNA as shown in SEQ ID NO: 9 and the corresponding amino acid sequence of the human CD80 protein is shown in SEQ ID NO: 10. The nucleotide sequence of the HLA-DR molecule, whether non-specific allele or specific allele is easily available from current technology and sequence databases.

The nucleic acid is "in a form suitable for expression of the HLA-DR and costimulatory molecules" in which the nucleic acid contains all of the coding and regulatory sequences required for transcription and translation of a gene, which may include promoters, enhancers and polyadenylation signals, and sequences necessary for transport of the molecule to the surface of the tumor cell, including N-terminal signal sequences. When the nucleic acid is a cDNA in a recombinant expression vector, the regulatory functions responsible for transcription and/or translation of the cDNA are often provided by viral sequences. Examples of commonly used viral promoters include those derived from polyoma, Adenovirus 2, cytomegalovirus and Simian Virus 40, and retroviral LTRs. Regulatory sequences linked to the cDNA can be selected to provide constitutive or inducible transcription, by, for example, use of an inducible promoter, such as the metallothienin promoter or a glucocorticoid-responsive promoter. Expression of the HLA-DR and costimulatory molecules on the surface of the tumor cell can be accomplished, for example, by including a native transmembrane coding sequence of the molecule, in the nucleic acid sequence, or by including signals which lead to modification of the protein, such as a C-terminal inositol-phosphate linkage, that allows for association of the molecule with the outer surface of the cell membrane.

A preferred approach for introducing nucleic acid encoding the HLA-DR and costimulatory molecules into the primary immune-privilege tumor cells is by use of a viral vector containing nucleic acid, e.g. a cDNA, encoding the HLA-DR and costimulatory molecules. Examples of viral vectors which can be used include retroviral vectors, adenoviral vectors and adeno-associated viral vectors. Infection of primary immune privilege tumor cells with a viral vector has the advantage that a large proportion of cells will receive nucleic acid, thereby obviating a need for selection of cells which have received nucleic acid, and molecules encoded within the viral vector, e.g. by a cDNA contained in the viral vector, are expressed efficiently in cells which have taken up viral vector nucleic acids.

Alternatively, the HLA-DR and costimulatory molecules can be expressed on a primary immune-privilege tumor cell using a plasmid expression vector which contains nucleic acid, e.g. a cDNA, encoding the HLA-DR and costimulatory molecules. Suitable plasmid expression vectors include CDM8 and pMT2PC. Since only a small fraction of cells (about 1 out of $10^5$) typically integrate transfected plasmid DNA into their genomes, it is advantageous to transfect a nucleic acid encoding a selectable marker into the tumor cell along with the nucleic acid(s) of interest. Preferred selectable markers include those which confer resistance to drugs such as G418, hygromycin and methotrexate. Selectable markers may be introduced on the same plasmid as the gene(s) of interest or may be introduced on a separate plasmid. Following selection of transfected primary immune-privilege tumor cells using the appropriate selectable marker(s), expression of the HLA-DR and costimulatory molecules on the surface of the tumor cell can be confirmed by immunofluorescent staining of the cells. For example, cells may be stained with a fluorescently labeled monoclonal antibody reactive against the HLA-DR and costimulatory molecules or with a fluorescently labeled soluble receptor which binds the HLA-DR and costimulatory molecules. Expression of the CD80 costimulatory molecule can be determined using a labeled soluble CD28 or CTLA4 protein or fusion protein which binds to CD80 can be used to detect expression of CD80.

When transfection of tumor cells leads to modification of a large proportion of the tumor cells and efficient expression of the HLA-DR and costimulatory molecules on the surface of tumor cells, e.g. when using a viral expression vector, tumor cells may be used without further isolation or subcloning. Alternatively, a homogeneous population of transfected tumor cells can be prepared by isolating a single transfected tumor cell by limiting dilution cloning followed by expansion of the single tumor cell into a clonal population of cells by standard techniques.

Fragments, mutants or variants of MHC class II molecules that retain the ability to bind peptide antigens and activate T cell responses, as evidenced by proliferation and/or lymphokine production by T cells, are considered within the scope of the invention.

When a tumor cell is transfected with multiple nucleic acid sequences that encode the co stimulatory molecule along with the MHC class II α chain protein and β chain protein, the transfections can be performed simultaneously or sequentially. If the transfections are performed simultaneously, the molecules can be introduced on the same nucleic acid, so long as the encoded sequences do not exceed a carrying capacity for a particular vector used. Alternatively, the molecules can be encoded by separate nucleic acids. If the transfections are conducted sequentially and primary immune-privilege tumor cells are selected using a selectable marker, one selectable marker can be used in conjunction with the first introduced nucleic acid while a different selectable marker can be used in conjunction with the next introduced nucleic acid.

The expression of MHC class II molecules on the cell surface of a primary immune-privilege tumor cell can be determined, for example, by immunoflourescence of tumor cells using fluorescently labeled monoclonal antibodies directed against different MHC class II molecules. Monoclonal antibodies which recognize either non-polymorphic regions of a particular MHC molecule (non-allele specific) or polymorphic regions of a particular MHC class II molecule (allele-specific) can be used are known to those skilled in the art.

Another aspect of the invention provides methods for increasing the immunogenicity of a tumor cell by modification of the tumor cell in vivo to express a costimulatory molecule and the MHC Class II molecules to trigger a primary, antigen-specific, signal in T cells. Primary immune-privilege tumor cells can be modified in vivo by introducing nucleic acid sequences encoding the CD4+ T cell costimulatory molecule and the MHC Class II proteins into the tumor cells in a form suitable for expression of the molecules on the surface of the tumor cells. In one embodiment, a recombinant expression vector is used to deliver the nucleic acid sequences. Vectors useful for in vivo gene therapy have been previously described and include retroviral vectors, adenoviral vectors and adeno-associated viral vectors. Alternatively, nucleic acid can be delivered to tumor cells in vivo by direct injection of naked nucleic acid into tumor cells. A delivery apparatus is commercially available (BioRad). Optionally, to be suitable for injection, the nucleic acid sequences can be complexed with a carrier such as a liposome.

In one embodiment, the tumor base cell vaccines are used to activate ex vivo and increase levels of activated CD4+ T cells. To practice the method of the invention, a source of T cells is obtained from a subject. The term subject is intended to include living organisms in which an immune response can be elicited, e.g., mammals. Examples of subjects include humans, dogs, cats, mice, rats, and transgenic species thereof. T cells can be obtained from a number of sources, including peripheral blood leukocytes, bone marrow, lymph node tissue, spleen tissue, and tumors. Preferably, peripheral blood leukocytes are obtained from an individual by leukopheresis. To isolate T cells from peripheral blood leukocytes, it may be necessary to lyse the red blood cells and separate peripheral blood leukocytes from monocytes by, for example, centrifugation through a PERCOLL™. gradient. A specific subpopulation of T cells, such as CD4+ or CD8+ T cells, can be further isolated by positive or negative selection techniques. For example, negative selection of a T cell population can be accomplished with a combination of antibodies directed to surface markers unique to the cells negatively selected. A preferred method is cell sorting via negative magnetic immunoadherence which utilizes a cocktail of monoclonal antibodies directed to cell surface markers present on the cells negatively selected. For example, to isolate CD4.+ cells, a monoclonal antibody cocktail typically includes antibodies to CD14, CD20, CD11b, CD 16, HLA-DR, and CD8.

The process of negative selection results in an essentially homogenous population of CD4+ or CD8+ T cells. The T cells can be activated as described herein, by contact with the tumor cell based vaccines of the present invention. Conditions appropriate for T cell culture include an appropriate media (e.g., Minimal Essential Media or RPMI Media 1640) which may contain factors necessary for proliferation and viability, including animal serum (e.g., fetal bovine serum) and antibiotics (e.g., penicillin streptomycin). The T cells are maintained under conditions necessary to support growth, for example an appropriate temperature (e.g., 37° C.) and atmosphere (e.g., air plus 5% $CO_2$) The rate of T cell proliferation and time for T cell stimulation can be monitored by assaying for the presence of cell surface molecules, such as B7-1, B7-2, which are induced on activated T cells. T cells expanded by the method of the invention can secrete high levels of cytokines (e.g., IL-2, IFNγ, IL-4, GM-CSF and TNFα.) into the culture supernatants. These cytokines can be purified from the culture supernatants or the supernatants can be used directly for maintaining cells in culture. Similarly, the T cells expanded by the method of the invention together with the culture supernatant and cytokines can be administered to support the growth of cells in vivo. For example, in patients with tumors, T cells can be obtained from the individual, expanded ex vivo and the resulting T cell population and supernatant, including cytokines can be readministered to the patient to augment T cell growth in vivo.

Another aspect of the invention is a composition of the modified primary immune-privilege tumor cells in a biologically compatible form suitable for pharmaceutical administration to a subject in vivo. This composition comprises an amount of modified primary immune-privilege tumor cells and a physiologically acceptable carrier. The amount of modified primary immune-privilege tumor is selected to be therapeutically effective. Examples of acceptable carriers include saline and aqueous buffer solutions. In all cases, the compositions must be sterile and must be fluid to the extent that easy syringability exists. The term "subject" is intended to include living organisms in which primary immune-privilege tumors can arise.

Administration of the therapeutic compositions of the present invention can be carried out using known procedures, at dosages and for periods of time effective to achieve the desired result. For example, a therapeutically effective dose of modified primary immune-privilege tumor cells may vary according to such factors as age, sex and weight of the individual, the type of tumor cell and degree of tumor burden, and the immunological competency of the subject. Dosage regimens may be adjusted to provide optimum therapeutic responses. For instance, a single dose of modified primary immune-privilege tumor cells may be administered or several doses may be administered over time. Administration may be by injection, including intravenous, intramuscular, intraperitoneal and subcutaneous injections.

Primary immune-privilege tumor cells can be obtained from a subject by, for example, surgical removal of such cells, e.g. a biopsy of the tumor. Tumor cells can be transfected immediately after being obtained from the subject or can be cultured in vitro prior to transfection to allow for further characterization of the tumor cells (e.g. determination of the expression of cell surface molecules). The nucleic acids chosen for transfection can be determined following characterization of the proteins expressed by the tumor cell. Primary immune-privilege tumor cells which express no MHC class II molecules are chosen and then these cells are transfected with nucleic acids encoding MHC Class II proteins.

Prior to administration to the subject, the modified primary immune-privilege tumor cells can be treated to render them incapable of further proliferation in the subject, thereby preventing any possible outgrowth of the modified primary immune-privilege tumor cells. Possible treatments include irradiation or mitomycin C treatment, which abrogate the proliferative capacity of the tumor cells while maintaining the ability of the tumor cells to trigger antigen-specific and costimulatory signals in T cells and thus to stimulate an immune response.

The modified primary immune-privilege tumor cells can be administered to the subject by injection of the tumor cells into the subject. The route of injection can be, for example, intravenous, intramuscular, intraperitoneal or subcutaneous. Administration of the modified primary immune-privilege tumor cells at the site of the original tumor may be beneficial for inducing T cell-mediated immune responses against the original tumor. Administration of the modified primary uveal melanoma tumor cells in a disseminated manner, e.g. by intravenous injection, may provide systemic anti-tumor immunity and, furthermore, may protect against metastatic spread of tumor cells from the original site. The modified primary immune-privilege tumor cells can be administered to a subject prior to or in conjunction with other forms of therapy or can be administered after other treatments such as chemotherapy or surgical intervention.

The modified primary immune-privilege tumor cells of the current invention may also be used in a method for preventing or treating metastatic spread of a tumor or preventing or treating recurrence of a tumor. Administration of modified primary immune-privilege tumor cells or modification of primary immune-privilege tumor cells in vivo as described herein can provide tumor immunity against cells of the original, unmodified tumor as well as metastases of the original tumor or possible regrowth of the original tumor.

This invention is further illustrated by the following examples which should not be construed as limiting. The examples set forth below use uveal melanoma cells but the methods and systems of the present invention may be used with any tumor cells derived from immune-privilege tissue. The contents of all references and published patents and patent applications cited throughout the application are hereby incorporated by reference Methods and Materials Cell Lines and Peripheral Blood Mononuclear Cells Cell lines. Primary uveal melanoma cell lines MEL202 and MEL270 and metastatic uveal melanoma cell line OMM2.3 were established from uveal melanoma patients and cultured as described for MEL202 (33,34). Sweig, Jurkat, and SUM159PT cells were maintained as described (34). H358 lung adenocarcinoma cells were obtained from the American Type Culture Collection (ATCC) and cultured as recommended by the ATCC.

Blood samples and peripheral blood mononuclear cells. Blood samples were obtained from healthy donors and uveal melanoma patients by venipuncture. Patient 308 was a 68-year-old male and blood was collected 6 months after enucleation of the right eye. Patient M-185 was a 45-year-old male whose left eye was enucleated in 1998. In January 2002, liver metastases were diagnosed, and in March to April 2002, he underwent segmental hepatectomy and insertion of an intrahepatic artery catheter and received four weekly courses of 100 mg/msq of intra-arterial fotemustine. In June 2002, he was inoculated with irradiated (18 Gy) autologous liver metastatic cells. Subsequent delayed type hypersensitivity responses to M-185 cells were negative. In October 2002, he presented with brain, liver, lung, and pelvic metastases. In January 2003, he was given dendritic cells loaded with M-185 cell lysates. He died in August 2003. Peripheral blood mononuclear cells (PBMC) used in the current study were obtained in January 2003 before dendritic cell inoculation. PBMCs were isolated from whole blood by Ficoll gradient, stored frozen in liquid nitrogen until used, and cultured as described previously (35). Thawed PBMCs that were >75% viable as measured by trypan blue exclusion were used. All cell lines and procedures with human materials were approved by the Institutional Review Boards of the participating institutions.

Human Leukocyte Antigen Typing

Cell lines and PBMCs were human leukocyte antigen (HLA) typed and analyzed using MicroSSP HLA class I and II ABDR DNA typing trays and analysis software (One Lambda, Inc.) according to the manufacturer's instructions. Genomic DNA was isolated from 4×106 cells using a DNeasy Tissue kit (Qiagen, Inc.) and amplified by PCR using recombinant Taq DNA polymerase (Fermentas, Inc.). HLA genotypes are referred to by their short-hand form (i.e., HLA- DRB1*0101 is DR1). FIG. 1A shows the HLA alleles of the PBMCs and cell lines used in these studies.

Retroviral Constructs, Transductions, and Drug Selection

The pLNCX2/DR1 and pLHCX/CD80 retroviral constructs, retrovirus production, transductions, and drug selections for DR1 (600 µg/mL G418; Sigma) and CD80 (75 µg/mL hygromycin; Calbiochem) were done as described (34). For example, for the pLNCX2/DR1 construct, DRα cDNA in the RSV.5 vector was PCR amplified including 5' NheI and 3' XhoI restriction sites: DRα 5' primer, TGTCGCTAGCATGGCCATAAGTGGAGT (SEQ ID NO: 1); and DRα 3' primer, ACTGCTCGAGTTACAGAGGC-CCC-CTGCGTT (SEQ ID NO: 2). The PCR product was cloned into the pCR2.1-TA vector (Invitrogen, Carlsbad, Calif.), excised with NheI and EcoRI, and inserted into the multiple cloning site (MCS)-A of NheI- and EcoRI-digested pIRES plasmid (Clontech, Palo Alto, Calif.). DRβ0101 in the RSV.5 vector was PCR amplified including 5' XmaI and 3' NotI sites and subcloned into the 5' XmaI and 3' NotI sites of the MCS-B of the pIRES vector: DRβ 0101 5' primer, AGTACCCGGGATGGTGTGTCTGAAGCTC (SEQ ID NO: 3); and DRβ 01013' primer, TAG-TGCGGCCGCT-CAGCTCAGGAATCCTGTTG (SEQ ID NO: 4). PCR conditions for both DRα and DRβ0101 amplifications were: denature at 94° C. for 2 min, denature at 94° C. for 1 min, anneal at 60.9° C. or 62.9° C. (DRA and DRB0101, respectively) for 1 min, extended at 72° C. for 3 min (High Fidelity Taq; Roche, Basel, Switzerland); repeat the last three steps 30 times and extend at 72° C. for 7 min. The resulting construct is pIRES/DR1 as shown in FIG. 7A.

The pLNCX2 retroviral vector (Clontech) was modified to include a linker containing an AvrII site in the MCS. To make the linker, equimolar amounts of the oligonucleotides 5'-GATCTCGAGCTCCTAGGAATTGTTTGGC-CGAGGC-3'(SEQ ID NO: 5) and 3'-AGCTCGAGGATCCT-TAACAAACCGGCTCCGCCGG-5' (SEQ ID NO: 6) were mixed, heated at 95° C. for 5 min, and then incubated at 22° C. for 1 h. The resulting linker was ligated to BglII- and NotI-digested pLNCX2. The resulting construct is pLNCX2/AvrII.

The DRA-IRES-DRB0101 fragment of the pIRES/DR1 was digested with NheI and NotI and gel purified using a QIAquick gel extraction kit (Qiagen, Valencia, Calif.) and then ligated to AvrII- and NotI-digested pLNCX2/AvrII. The final MHC class II construct is pLNCX2/DR1 as shown in FIG. 7A.

For the pLHCX/CD80(HPH) construct, pLHCX (hygromycin resistance; Clontech) was modified to include a 5' BamHI site and a 3' HindIII site by inserting an oligonucleotide linker between the HindIII and ClaI sites of the MCS. The original HindIII in the vector was deleted by insertion of the linker. XhoI, HpaI, AvrII, and NotI restriction sites were included in the linker for future cloning purposes. The linker sequence was: L1, 5'-AGCTGCTCGAGTTAACGGATC-CTAGGAAGCTTGCGGCCGCAT-3' (SEQ ID NO: 7); and L2, 5'-CGATGCGGCCGCAAGCTTCCTAGGATC-CGTTAACTCGAGC-3' (SEQ ID NO: 8).

Human CD80 was excised from the pREP10/B7.1 vector with BamHI and HindIII and inserted into the modified pLHCX vector using the BamHI and HindIII sites as shown in FIG. 7B.

Cells.

Media for all cell lines contained 1% gentamicin, 1% penicillin/streptomycin (all from BioSource, Rockville, Md.), and 2 mM Glutamax (BRL/Life Sciences, Grand Island, N.Y.). All cells and T-cell activation assays were cultured at 37° C. in 5% CO2. SUM159PT was obtained from the Michigan Breast Cell/Tissue Bank and was maintained in Ham's F-12 medium with 10% heat-inactivated FCS (Hyclone, Logan, Utah), 1 µg/ml hydrocortisone, and 5 µg/ml insulin (both from Sigma, St. Louis, Mo.). Mel 202 (33) was grown in RPMI 1640 (BioSource, Rockville, Md.) with 10% FCS, 0.01 M HEPES (Invitrogen, Grand Island, N.Y.), and $5 \times 10^{-5}$ M β-mercaptoethanol (J. T. Baker, Inc., Phillipsburg, N.J.). Transductants were grown in the same medium as their parental cells, supplemented with G418 (Sigma), puromycin (Clontech, Palo Alto, Calif.), or hygromycin (Calbiochem, San Diego, Calif.; depending on their transgenes. Sweig and Jurkat cells were obtained from the American Type Culture Collection and were maintained in Iscove's modified Dulbecco's medium (BioSource) supplemented with 10% fetal clone I (FBP; Hyclone). Peripheral blood mononuclear cells (PBMCs) were grown in Iscove's modified Dulbecco's medium with 5% human AB serum (Gemini Bio-Products, Woodland, Calif.). All cell lines and procedures with human materials were approved by the Institutional Review Boards of the participating institutions.

Retrovirus Production.

293T cells (obtained from the Harvard Gene Therapy Institute) were plated in a 6-cm dish at $9 \times 10^5$ cells/4 ml of 293T medium [DMEM (BioSource, Rockville, Md.), 1% gentamicin, 1% penicillin/streptomycin, 1% Glutamax, and 10% heat-inactivated FCS] and cultured at 37° C. Twenty h later, the growth medium was replaced with 4 ml of 37° C. Iscove's modified Dulbecco's medium containing 25 mM HEPES (BioSource), 1% Glutamax, and 10% heat-inactivated FCS. Three h later, the 293T cells were transfected with pLNCX2/DR0101 and pLHCX/CD80 plasmids (8 µg) plus pMD. MLV gag.pol (6 µg) and pMD.G (2 µg) using CaPO4. Twelve to 16 h after transfection, medium was replaced with 293T growth medium containing 10 mM HEPES. Virus was collected 48 h later and either used immediately or stored at −80° C.

Retroviral Transduction.

Tumor cells were plated in 6-well plates at $1.2-3 \times 10^5$ cells/3 ml growth medium/well. Approximately 16 h after plating, when cells were in log phase, growth medium was replaced with 500 µl of viral supernatant mixed with 500 µl of 293T medium containing 4 µg/ml polybrene (Sigma) and 10 mM Hepes. Cells were incubated for 5-6 hrs at 37° C., washed twice with excess PBS and maintained in growth medium for 2 days before adding G418, puromycin, and/or hygromycin. Transduced cells were grown in the same medium as their parental cells.

Peptides, Antibodies, Reagents, and Immunofluorescence

DR1-restricted HER2/neu peptide 776 to 790 (GVG-SPYVSRLLGICL; refs. 36, 37) was synthesized at the University of Maryland Biopolymer Laboratory. HLA-DR-phycoerythrin (PE), CD80-PE, and FITC and PE isotype (mouse IgG2a) control monoclonal antibodies (mAb) were purchased from BD PharMingen; goat anti-mouse IgG-FITC from ICN; c-neu (Ab-2) from Oncogene; CD4-FITC and CD8-FITC from Miltenyi Biotech; and CD3-PE from eBioscience. Ii mAb PIN1.1 was prepared, and tumor cells and PBMCs were stained and analyzed by flow cytometry as described (34).

Western Blots

Western blot analyses for Ii were done as described (28, 35) using culture supernatant from hybridoma PIN1.1 at a 1:100 dilution followed by sheep anti-mouse-horseradish peroxidase (Amersham) at a 1:10,000 dilution.

IFNγ Treatment

Tumor cells were incubated for 48 h in culture medium supplemented with 100 units/mL recombinant human IFNγ (Pierce Biotechnology) and washed with culture medium to remove IFNγ.

T-Cell Priming with HER2/neu Peptide

PBMCs were thawed and resuspended in T-cell medium, and viability was determined by trypan blue exclusion. Viable PBMCs were plated at 1×107/4 mL T-cell medium/well in six-well plates with 2 μg/mL HER2/neu peptide 776 and incubated at 37° C. and 5% CO2. After 5 days, nonadherent cells were harvested, washed twice with T-cell medium, counted, and plated at 1×106/2 mL T-cell medium/well in 24-well plates with 20 units/mL recombinant human interleukin (IL)-2 (R&D Systems). Seven days later, nonadherent cells were harvested, washed, counted, and plated at 1×106/2 mL T-cell medium/well without exogenous IL-2 and used the following day.

HER2/neu Antigen Presentation Assays

HER2/neu antigen presentation assays were done as described (35) with the following modifications: for endogenous HER2/neu presentation, stimulator cells (2.5×104 per well) and HER2/neu peptide 776-primed PBMCs (5×104 per well) in 200 μL/well T-cell medium were cultured at 37° C. and 5% CO2. After 48 h, the 96-well plate were spun at 1,200 rpm for 3 min, and the supernatants were assayed for IFNγ by ELISA. Values are the averages of triplicate data points with their SD. For exogenous HER2/neu peptide presentation, HER2/neu peptide 776 at 2 μg/mL was added to each well at the beginning of the 2-day culture period.

PBMC Priming and Boosting with MHC II Tumor Cell Vaccines

PBMCs (2.5×106) were mixed with irradiated (10,000 Rads) transductants or parental tumor cells (2.5×105) and cultured in 2 mL T-cell medium/well in 24-well plates at 37° C. and 5% CO2. After 3 days of culture, nonadherent cells were harvested, washed twice, and replated with 20 units/mL IL-2 in 24-well plates at 1×106/2 mL T-cell medium. Five days later, nonadherent cells were harvested, washed, and plated at 1×106/2 mL T-cell medium/well without IL-2 for an additional day. The resulting "primed" cells were then boosted with live transductants or parental cells as described (35) at a ratio of 1:2 boosting cells/PBMCs. PBMCs were depleted for CD8+ or CD4+ T cells as described (34, 35), except depletions were done on day 0 before priming. For experiments with patients' PBMCs, the same protocol was used except recombinant human IL-15 (20 ng/mL; PeproTech) was used instead of IL-2.

Statistical Analysis

SD and Student's t test were calculated using Excel version 2002.

Example I

Primary and metastatic uveal melanoma MHC II vaccines. MHC II vaccines should only express MHC II but not express Ii to allow endogenous tumor peptides within the endoplasmic reticulum access to the peptide binding groove of MHC II molecules. Because the MHC II and Ii genes are coordinately regulated by the MHC II transactivator (CIITA; ref. 38), tumor cells that constitutively express MHC II, or are induced by IFNγ to express MHC II, also express Ii and are not suitable for vaccine development. Conveniently, some uveal melanomas methylate the CIITA gene, preventing expression of either MHC II or Ii (39). To identify uveal melanoma cell lines that cannot be stimulated to express either MHC II or Ii, uveal melanoma cell lines derived from primary tumors (MEL202 and MEL270) or from liver metastasis (OMM2.3) were cultured with or without 100 units/mL recombinant human IFNγ. Cell surface expression of MHC I and MHC II was analyzed by flow cytometry as shown in FIG. 1B and expression of Ii was analyzed by Western blotting as shown in FIG. 1C. Both primary and metastatic uveal melanoma cell lines expressed MHC I but did not express MHC II and were not induced by IFNγ to express either MHC II or Ii as shown in FIGS. 1B and 1C respectively. Therefore, these cell lines are suitable candidates for MHC II vaccine development.

Figure 2:
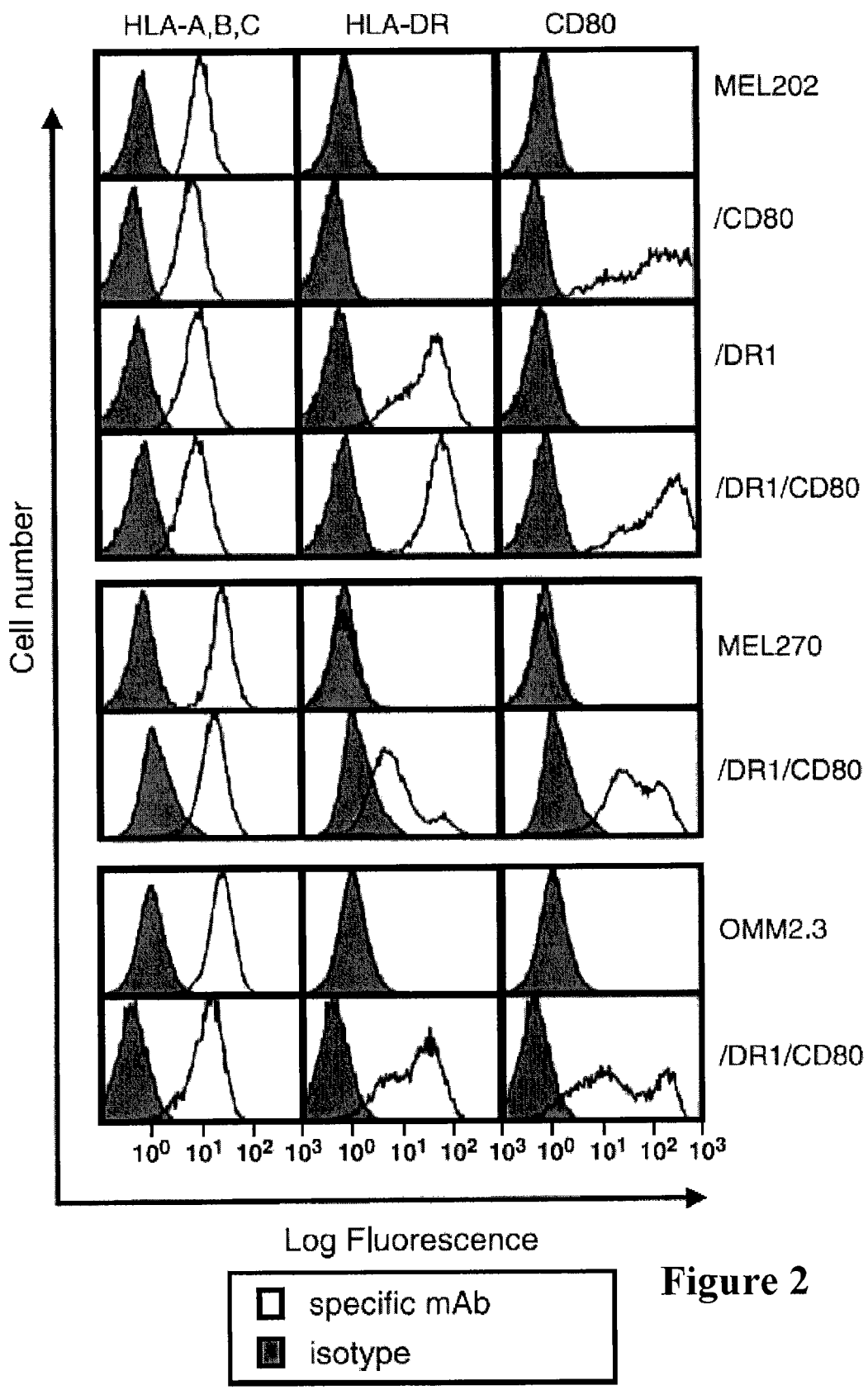
FIG. 2 shows that primary (MEL202 and MEL270) and metastatic (OMM2.3) uveal melanoma cells transduced with HLA-DR and/or CD80 genes express HLA-DR and/or CD80 on the cell surface. Live transductants were stained for plasma membrane MHC I (mAb W6/32-PE), HLA-DR (mAb L243-PE), or CD80 (CD80-PE).

MHC II vaccine cells were generated by transducing the primary and metastatic uveal melanoma cell lines with retroviruses encoding HLA-DRB1*0101 (DR1) and/or the costimulatory molecule CD80. The transductants have maintained stable expression of their transgenes in culture for >6 months. Therefore, vaccine cells prepared from the primary (MEL202/DR1/CD80 and MEL270/DR1/CD80) and metastatic (OMM2.3/DR1/CD80) uveal melanoma cell lines stably express the transduced DR1 and CD80 genes but do not express Ii as shown in FIG. 2.

Example II

Figure 3A:
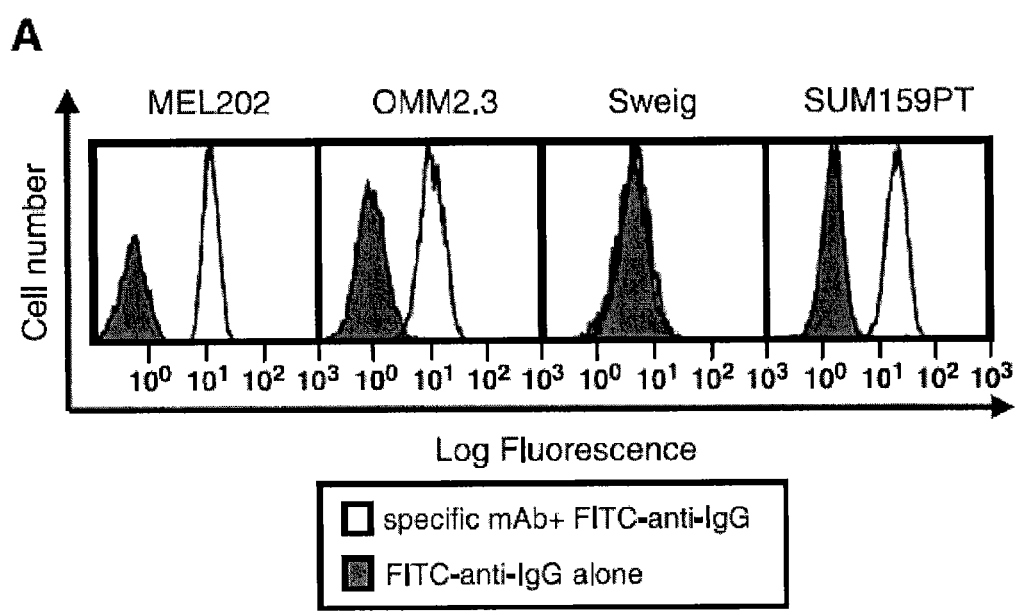
FIGS. 3A and B show that primary (MEL202 and MEL270) and metastatic (OMM2.3) uveal melanoma cells express HER2/neu and activate HER2/neu peptide-primed T cells. A, live uveal melanoma cells were stained for plasma membrane HER2/neu (mAb c-neu-Ab2). SUM159PT and Sweig cells are HER2/neu+ and HER2/neu− control cells, respectively. B, HLA-DR1-restricted, HER2/neu-p776 peptide-primed T cells were cocultured with live MEL202 or OMM2.3 parental cells or transductants. Exogenous HER2/neu p'776 was added to some wells. T-cell activation was quantified by measuring IFNγ release. Data for each panel are representative of two independent experiments with donor 1 PBMC.
Figure 3B:
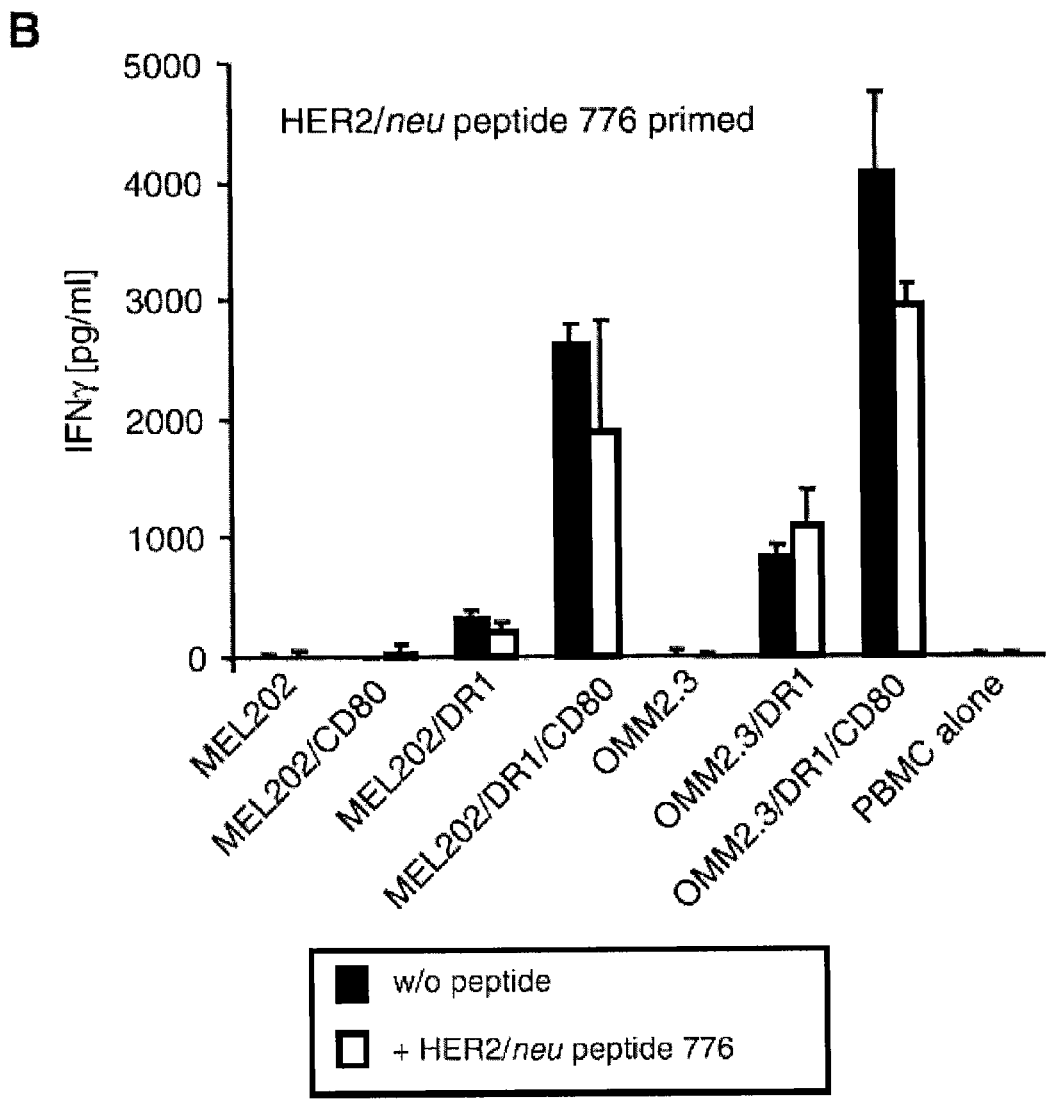

Vaccine cells express functional MHC II molecules that present endogenously synthesized tumor peptides. To ascertain that the transduced HLA-DR1 molecules of the vaccine cells are functional, DR1+ PBMCs from healthy donor 1 were primed to HER2/neu peptide 776 and boosted with MEL202/DR1/CD80 or OMM2.3/DR1/CD80 vaccine cells, which constitutively express HER2/neu. MEL202/DR1/CD80 and OMM2.3/DR1/CD80 vaccine cells boost HER2/neu-primed PBMC, which produce IFNγ as shown in FIG. 3B. DR1 is the functional restriction element for the response because DR1-parental cells (MEL202 or OMM2.3) are not effective. Coexpression of CD80 by the vaccine cells enhances antigen presentation because transductants without CD80 (MEL202/DR1 or OMM2.3/DR1) are not as effective APC as vaccine cells expressing both DR1 and CD80 as shown in FIG. 3B. Although the vaccine cells are MHC I allogeneic with respect to the PBMC, there is no allogeneic response because MEL202/CD80 cells do not activate T cells. Therefore, the transduced DR1 molecules of the uveal melanoma vaccines are functional antigen presentation elements for endogenously synthesized tumor peptides.

Example III

MHC II+CD80+ Vaccine Cells Made from Primary Uveal Melanomas Prime and Boost Naive CD4+ T Cells.

Figure 4A:
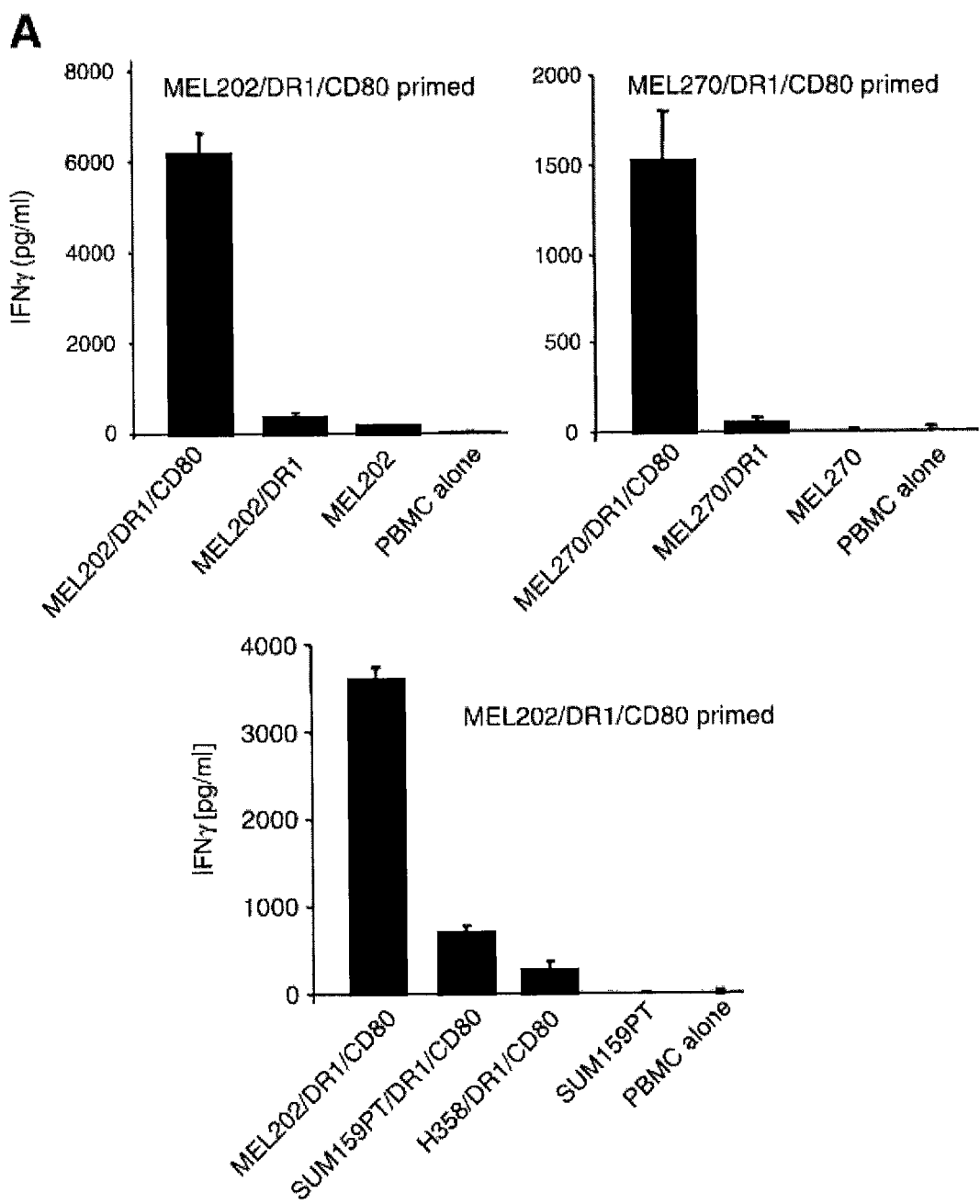
FIGS. 4A, B and C show that MHC II vaccines prepared from primary uveal melanoma cells prime and boost tumor-reactive CD4+ T cells. A, PBMCs from donor 1 were primed with MEL202/DR1/CD80 or MEL270/DR1/CD80 cells and boosted with the indicated transductants or parental cells. B, PBMCs were primed with MEL202/DR1/CD80, MEL202/DR1, or MEL202 cells and boosted with the indicated MEL202 parental cells or transductants. C, PBMCs were nondepleted or depleted for CD8+ or CD4+ T cells before priming and boosting with MEL202/DR1/CD80 vaccine cells. PBMCs were >99% depleted for CD8+ T cells and >98% depleted for CD4+ T cells throughout the course of the experiment. Nondepleted PBMCs secreted 5.2±0.37 ng/mL IFNγ. Percentage IFNγ response is relative to the response of undepleted PBMC, which was set at 100%. T-cell activation for all panels was quantified by measuring IFNγ release. Data for each panel are representative of three or more independent experiments with PBMC from donors 1, 2, or 3.
Figures 4B, 4C:
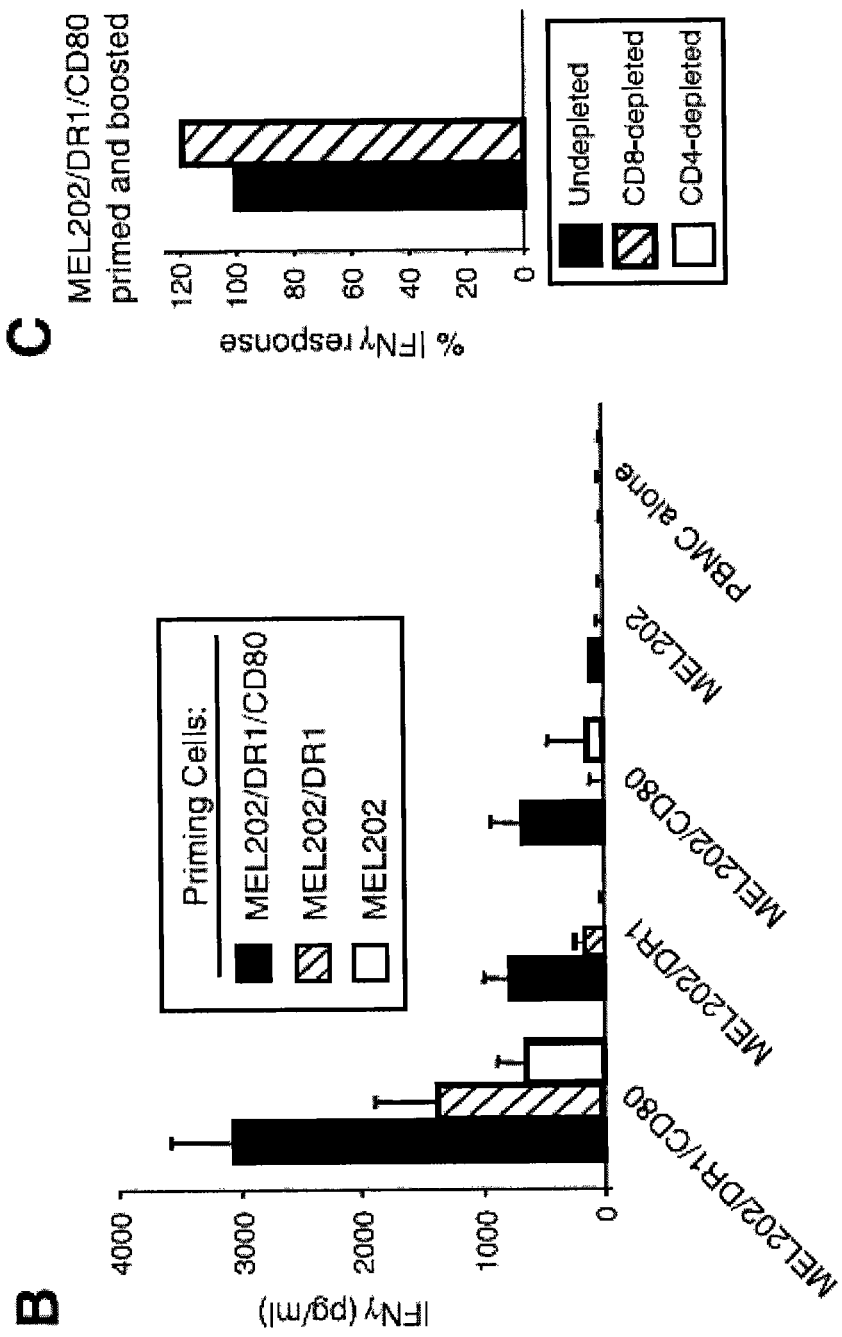

The MHC II vaccines are designed to prime naive CD4+ T cells to novel, endogenously synthesized tumor antigens. To determine if the vaccines have this capability, DR1+ PBMCs from healthy donor 1 were cocultured (primed) with irradiated vaccine cells prepared from primary uveal melanomas (MEL202/DR1/CD80 or MEL270/DR1/CD80) and boosted with either parental or transduced uveal melanoma cells. Vaccines prepared from mammary carcinoma (SUM159PT/DR1/CD80; ref. 34) and lung adenocarcinoma (H358/DR1/CD80; ref. 5) were also used as boosting agents to determine specificity of the activated CD4+ T cells for uveal melanoma cells and to control for potential alloreactivity. Priming and boosting with either uveal melanoma vaccine induced significant IFNγ release as shown in FIG. 4A. Activated T cells were highly specific for uveal melanoma cells and minimally reactive with breast and lung cancer cells. The minimal reactivity to breast and lung cells could be due to cross-reactivity to shared DR1-restricted antigens, such as HER2/neu, which are expressed by SUM159PT and H358 cells. Vaccine cell coexpression of CD80 enhanced the response, which was DR1 restricted, because transductants without CD80 or DR1 induced significantly less IFNγ as shown in FIG. 4B. Despite the potential for alloreactivity against HLA-A3, which is expressed by the priming MEL202/DR1/CD80 cells and boosting H358/DR1/CD80 cells, the minimal reactivity with the lung cancer cells indicates that the vaccines do not stimulate a significant alloresponse. Similar results were obtained with PBMC from donors 2 and 3 (data not shown).

To identify the activated cells, PBMCs from healthy donor 1 were depleted for either CD4+ or CD8+ T cells before priming with MEL202/DR1/CD80 vaccine cells. By viewing FIG. 4C it is evident that depletion of CD4+ T cells virtually eliminated IFNγ release, whereas depletion of CD8+ T cells had no effect. Thus, and surprisingly the MHC II-matched allogeneic uveal melanoma cells, expressing CD80 and HLA-DR alleles matched to the responding T cells, efficiently prime and boost healthy donor CD4+ T cells that are specific for uveal melanoma tumor cells.

Example IV

Vaccines Made from Metastatic Uveal Melanomas are Less Efficient Activators of CD4+ T Cells.

Figure 5A:
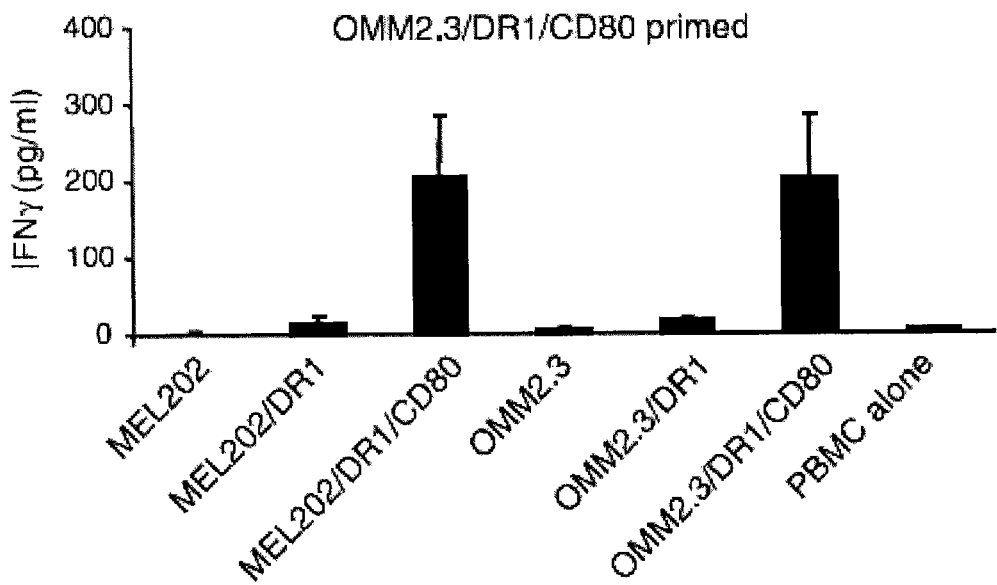
FIGS. 5A, B, C and D show that MHC II uveal melanoma vaccines prepared from primary tumor cells prime and boost T cells that cross-react with primary and metastatic cells and are more effective than vaccines prepared from metastatic uveal melanoma cells. PBMCs from donor 1 were primed with A, OMM2.3/DR1/CD80; B, MEL270/DR1/CD80 or OMM2.3/DR1/CD80; C, MEL202/DR1/CD80; or D, MEL270/DR1/CD80 vaccine cells and boosted with the indicated transductants or parental cells. Data for each panel are representative of three independent experiments with PBMC from donors 1, 2, or 3. *, P<0.02, statistically significantly different values.
Figure 5B:
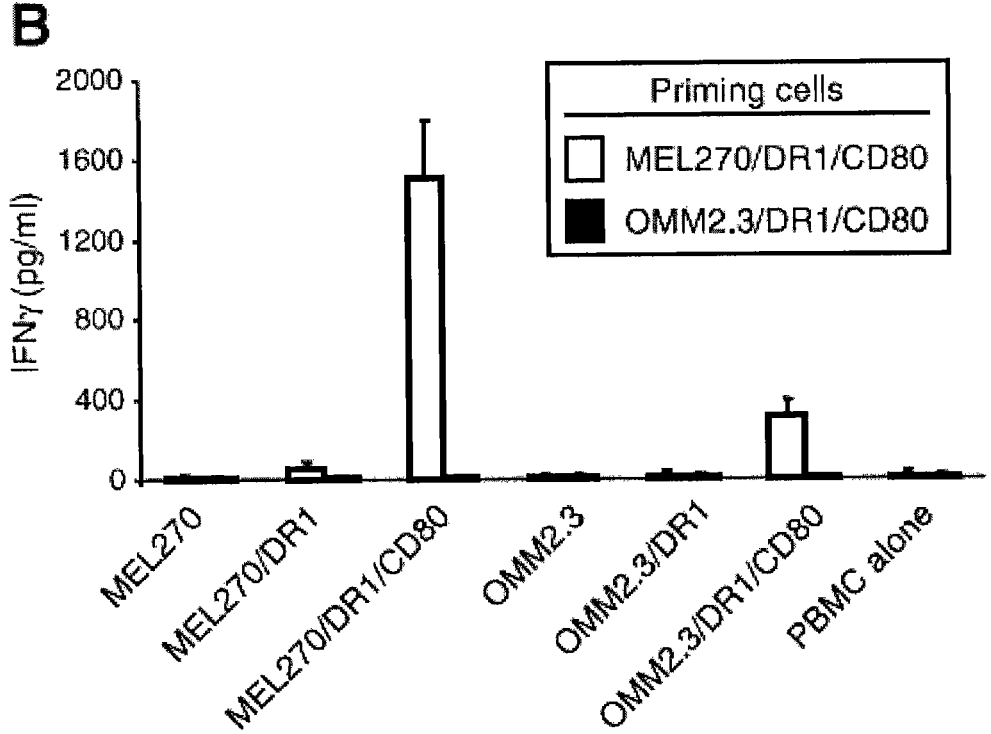

If the efficacy of the uveal melanoma vaccines prepared from primary tumors is due to their origin in the immune-privileged eye, then MHC II+CD80+ vaccines prepared from metastatic uveal melanoma cells may be less capable of activating CD4+ T cells. This hypothesis was tested using transductants prepared from metastatic OMM2.3 cells, which are derived from a liver metastasis of the same patient from which the primary MEL270 line was derived. Priming with OMM2.3/DR1/CD80 and boosting with OMM2.3/DR1/CD80 or MEL202/DR1/CD80 cells repeatedly gave <10% the amount of IFNγ as priming and boosting with MEL202/DR1/CD80 as shown in FIG. 5A. The inability of the metastatic transductants to prime T cells could be due to individual variation between uveal melanoma patients 202 and 270. To eliminate this possibility, PBMC from DR1+ healthy donor 1 were primed in parallel with MEL270/DR1/CD80 or OMM2.3/DR1/CD80 transductants and boosted with MEL270/DR1/CD80 or OMM2.3/DR1/CD80. Although priming with MEL270/DR1/CD80 vaccines induced IFNγ release, no IFNγ was detectable following priming with metastatic OMM2.3/DR1/CD80 cells, and only very low levels of IFNγ were produced following priming with MEL270/DR1/CD80 and boosting with the metastatic cells as shown in FIG. 5B. Therefore, vaccines prepared from metastatic uveal melanoma cells are much less effective for activating T cells than vaccines prepared from primary uveal melanomas.

Example V

Uveal Melanoma Vaccines Prime and Boost CD4+ T Cells that Cross-React with Metastatic and Other Primary Uveal Melanomas.

If vaccines prepared from primary tumor cells are to be useful clinically, then they must prime CD4+ T cells that cross-react with metastatic tumor cells. To determine if the MHC II uveal melanoma vaccines have the capability to induce cross-reactivity, DR1+ PBMCs from healthy donor 1 were primed with MEL202/DR1/CD80 (FIG. 5C) or MEL270/DR1/CD80 (FIG. 5D) vaccine cells and boosted with MEL202, MEL270, or OMM2.3 transductants. Both vaccines prepared from primary tumor cells primed T cells that cross-react with metastatic tumor and with the other primary tumor cells. Similar results were obtained with PBMC from healthy donors 2 and 3 (data not shown). Importantly and surprisingly, vaccines made of primary uveal melanoma cells prime and boost T cells that are cross-reactive with other primary cells and with metastatic uveal melanoma cells.

Example VI

MHC II Uveal Melanoma Vaccines Prime and Boost T Cells from Patients with Primary and Metastatic Uveal Melanoma.

Figure 6A:
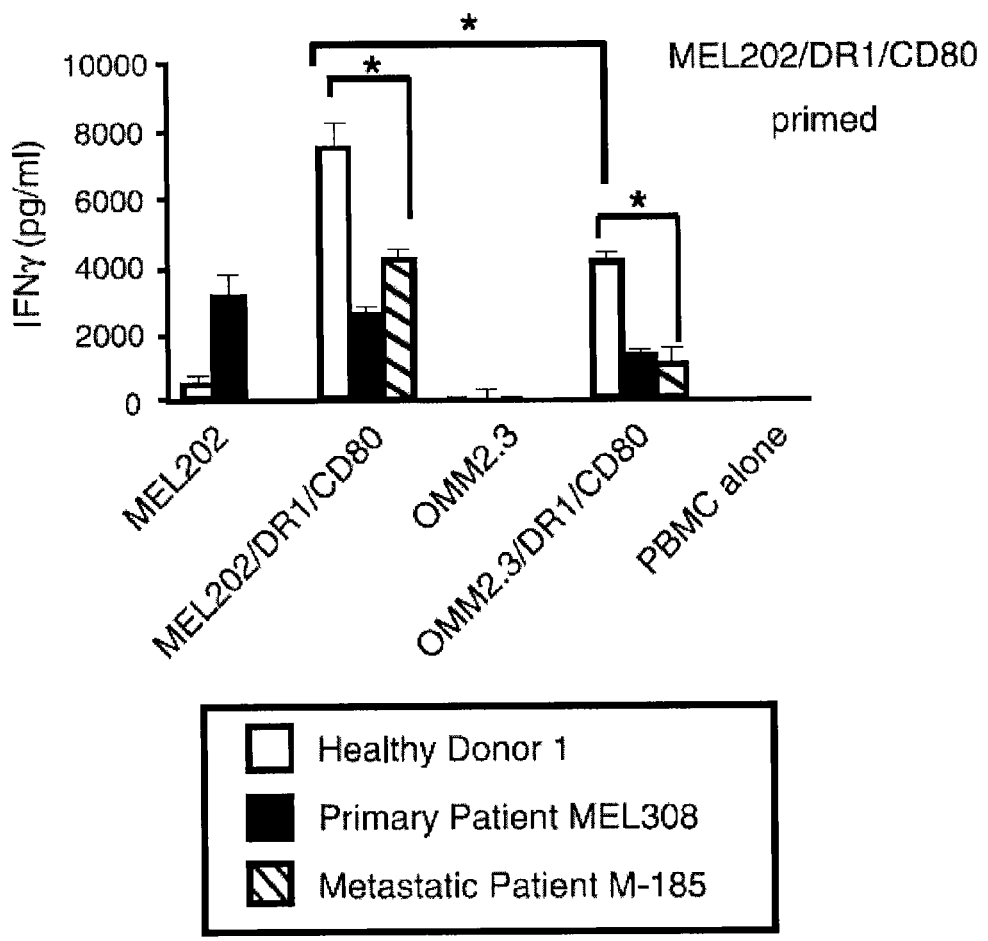
FIGS. 6A and B show that MHC II uveal melanoma vaccines prime and boost tumor-reactive T cells from primary and metastatic uveal melanoma patients. A, PBMCs from donor 1, from patient 308 with primary uveal melanoma, or from patient M-185 with uveal melanoma liver metastases were primed with MEL202/DR1/CD80 vaccine cells and boosted with MEL202 or OMM2.3 parental cells or transductants. *, P<0.03, statistically significantly different values. Data are representative of two independent experiments. B, MHC II "cocktail" vaccine strategy. MHC II uveal melanoma vaccines will be made from a panel of primary uveal melanoma cell lines that are transduced with the CD80 costimulatory molecule and one of the most common HLA-DR alleles. The vaccine for an individual patient can be "customized" by combining individual transductants expressing one or more of the HLA-DR alleles of the patient's MHC II haplotype. This "cocktail" of diverse uveal melanoma cells increases the variety of tumor antigen epitopes presented and increases the chance of activating patients' T cells to tumor peptides shared with their tumor cells.
Figure 6B:
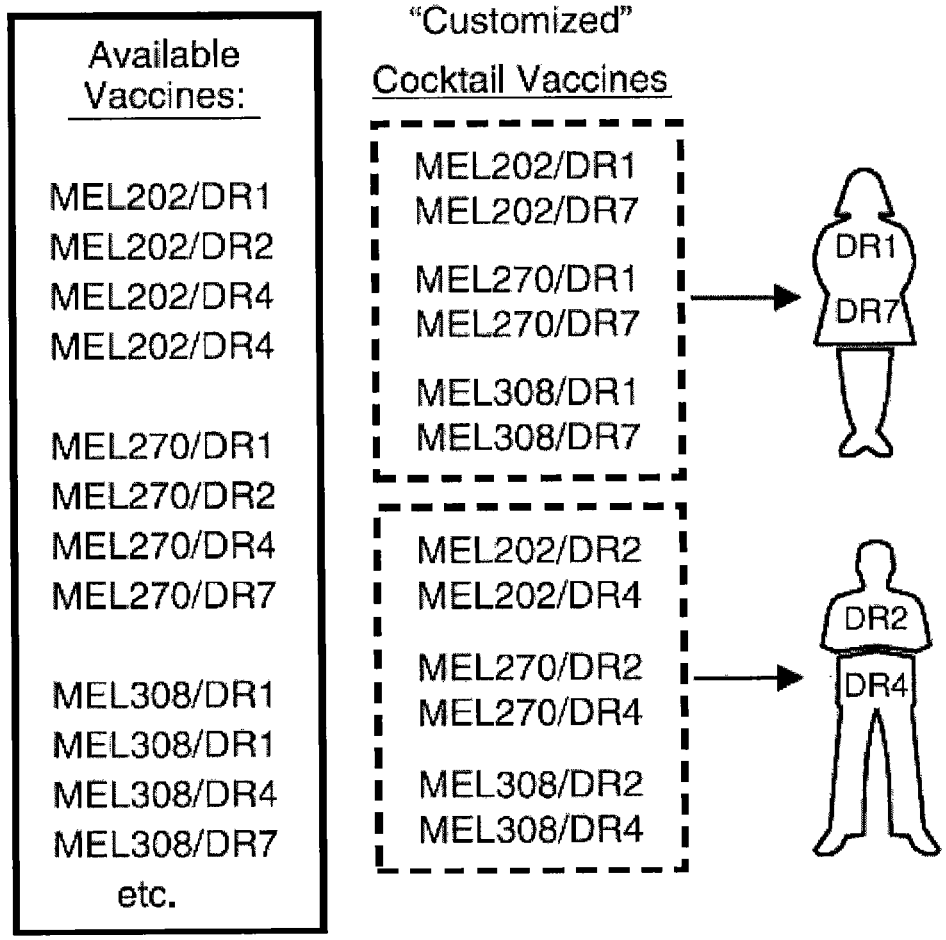

To determine if the vaccines prime T cells from the blood of uveal melanoma patients, MEL202/DR1/CD80 vaccine cells were cocultured with DR1+ PBMCs from (a) a patient with primary uveal melanoma (patient 308); (b) a patient with metastatic uveal melanoma (patient M-185); or (c) healthy donor 1. PBMCs were collected from patient 308 6 months after enucleation of the tumor-bearing eye when he had no clinically detectable metastatic disease. Patient M-185 had extensive metastatic disease of the liver at the time the PBMCs were collected. Priming and boosting with the primary MEL202/DR1/CD80 vaccine maximally activated PBMC from all donors, with the healthy donor giving the highest level of IFNγ as shown in FIG. 6A. Priming with MEL202/DR1/CD80 and boosting with the metastatic OMM2.3/DR1/CD80 vaccine similarly activated PBMC from the healthy donor and the two patients; however, the level of activation for all three donors was reduced relative to boosting with the primary vaccine. Therefore, MHC II+CD80+ uveal melanoma cell vaccines activate T cells from either healthy donors or uveal melanoma patients, and vaccines prepared from primary tumors are the most effective.

REFERENCES

All references cited herein are hereby incorporated by reference herein for all purposes.
1. Albert D M, Niffenegger A S, Willson J K. Treatment of metastatic uveal melanoma: review and recommendations. *Surv Ophthalmol* 1992; 36:429-38.
2. Harbour J. Clinical overview of uveal melanoma: introduction to tumors of the eye. In: Albert D M, Polans A, editors. *Ocular Oncology*. Marcel Dekker; 2003.
3. Kujala E, Makitie T, Kivela T. Very long-term prognosis of patients with malignant uveal melanoma. Invest Ophthalmol Vis Sci 2003; 44:4651-9.
4. Mooy C M, De Jong P T. Prognostic parameters in uveal melanoma: a review. *Surv Ophthalmol* 1996; 41:215-28.
5. Peters S, Voelter V, Zografos L, et al. Intra-arterial hepatic fotemustine for the treatment of liver metastases from uveal melanoma: experience in 101 patients. *Ann Oncol* 2006; 17:578-83.
6. Noter S L, Rothbarth J, Pijl M E, et al. Isolated hepatic perfusion with high-dose melphalan for the treatment of uveal melanoma metastases confined to the liver. *Melanoma Res* 2004; 14:67-72.
7. Staveley-O'Carroll K, Sotomayor E, Montgomery J, et al. Induction of antigen-specific T cell anergy: an early event in the course of tumor progression. *Proc Natl Acad Sci USA* 1998; 95:1178-83.
8. Niederkorn J Y. See no evil, hear no evil, do no evil: the lessons of immune privilege. *Nat Immunol* 2006; 7:354-9.
9. Streilein J W. Ocular immune privilege: therapeutic opportunities from an experiment of nature. *Nat Rev Immunol* 2003; 3:879-89.

10. Wang J C, Livingstone A M. Cutting edge: CD4+ T cell help can be essential for primary CD8+ T cell responses in vivo. *J Immunol* 2003; 171:6339-43.

11. Kern D E, Klarnet J P, Jensen M C, Greenberg P D. Requirement for recognition of class II molecules and processed tumor antigen for optimal generation of syngeneic tumor-specific class I-restricted CTL. *J Immunol* 1986; 136:4303-10.

12. Ossendorp F, Mengede E, Camps M, Filius R, Melief C J. Specific T helper cell requirement for optimal induction of cytotoxic T lymphocytes against major histocompatibility complex class II negative tumors. *J Exp Med* 1998; 187:693-702.

13. Ostrand-Rosenberg S, Thakur A, Clements V. Rejection of mouse sarcoma cells after transfection of MHC class II genes. *J Immunol* 1990; 144:4068-71.

14. Bennett S R, Carbone F R, Karamalis F, Miller J F, Heath W R. Induction of a CD8+ cytotoxic T lymphocyte response by cross-priming requires cognate CD4+ T cell help. *J Exp Med* 1997; 186:65-70.

15. Keene J A, Forman J. Helper activity is required for the in vivo generation of cytotoxic T lymphocytes. *J Exp Med* 1982; 155:768-82.

16. Bennett S R, Carbone F R, Karamalis F, Flavell R A, Miller J F, Heath W R. Help for cytotoxic-T-cell responses is mediated by CD40 signalling. *Nature* 1998; 393:478-80.

17. Ridge J P, Di Rosa F, Matzinger P. A conditioned dendritic cell can be a temporal bridge between a CD4+ T-helper and a T-killer cell. *Nature* 1998; 393:474-8.

18. Schoenberger S P, Toes R E, van der Voort E I, Offringa R, Melief C J. T-cell help for cytotoxic T lymphocytes is mediated by CD40-40L interactions. *Nature* 1998; 393:480-3.

19. Shedlock D J, Shen H. Requirement for CD4 T cell help in generating functional CD8 T cell memory. *Science* 2003; 300:337-9.

20. Janssen E M, Lemmens E E, Wolfe T, Christen U, von Herrath M G, Schoenberger S P. CD4+ T cells are required for secondary expansion and memory in CD8+ T lymphocytes. *Nature* 2003; 421:852-6.

21. Grakoui A, Shoukry N H, Woollard D J, et al. HCV persistence and immune evasion in the absence of memory T cell help. *Science* 2003; 302:659-62.

22. Sun J C, Bevan M J. Defective CD8 T cell memory following acute infection without CD4 T cell help. *Science* 2003; 300:339-42.

23. Ganss R, Arnold B, Hammerling G J. Mini-review: overcoming tumor-intrinsic resistance to immune effector function. *Eur J Immunol* 2004; 34:2635-41.

24. Qin Z, Blankenstein T. CD4+ T cell-mediated tumor rejection involves inhibition of angiogenesis that is dependent on IFNγ receptor expression by nonhematopoietic cells. *Immunity* 2000; 12:677-86.

25. Ostrand-Rosenberg S, Pulaski B A, Clements V K, Qi L, Pipeling M R, Hanyok L A. Cell-based vaccines for the stimulation of immunity to metastatic cancers. *Immunol Rev* 1999; 170:101-14.

26. Armstrong T D, Clements V K, Martin B K, Ting J P, Ostrand-Rosenberg S. Major histocompatibility complex class II-transfected tumor cells present endogenous antigen and are potent inducers of tumor-specific immunity. *Proc Natl Acad Sci USA* 1997; 94:6886-91.

27. Armstrong T D, Clements V K, Ostrand-Rosenberg S. MHC class II-transfected tumor cells directly present antigen to tumor-specific CD4+ T lymphocytes. *J Immunol* 1998; 160:661-6.

28. Qi L, Rojas J M, Ostrand-Rosenberg S. Tumor cells present MHC class II-restricted nuclear and mitochondrial antigens and are the predominant antigen presenting cells in vivo. *J Immunol* 2000; 165:5451-61.

29. Dolan B P, Gibbs K D, Jr., Ostrand-Rosenberg S. Tumor-specific CD4+ T cells are activated by "cross-dressed" dendritic cells presenting peptide-MHC class II complexes acquired from cell-based cancer vaccines. *J Immunol* 2006; 176:1447-55.

30. Muntasell A, Carrascal M, Alvarez I, et al. Dissection of the HLA-DR4 peptide repertoire in endocrine epithelial cells: strong influence of invariant chain and HLA-DM expression on the nature of ligands. *J Immunol* 2004; 173:1085-93.

31. Baskar S, Glimcher L, Nabavi N, Jones R T, Ostrand-Rosenberg S. Major histocompatibility complex class II+B7-1+ tumor cells are potent vaccines for stimulating tumor rejection in tumor-bearing mice. *J Exp Med* 1995; 181:619-29.

32. Pulaski B A, Ostrand-Rosenberg S. Reduction of established spontaneous mammary carcinoma metastases following immunotherapy with major histocompatibility complex class II and B7.1 cell-based tumor vaccines. *Cancer Res* 1998; 58:1486-93.

33. Verbik D J, Murray T G, Tran J M, Ksander B R. Melanomas that develop within the eye inhibit lymphocyte proliferation. *Int J Cancer* 1997; 73:470-8.

34. Dissanayake S K, Thompson J A, Bosch J J, et al. Activation of tumor-specific CD4(+) T lymphocytes by major histocompatibility complex class II tumor cell vaccines: a novel cell-based immunotherapy. *Cancer Res* 2004; 64:1867-74.

35. Thompson J A, Dissanayake S K, Ksander B R, Knutson K L, Disis M L, Ostrand-Rosenberg S. Tumor cells transduced with the MHC class II transactivator and CD80 activate tumor-specific CD4+ T cells whether or not they are silenced for invariant chain. *Cancer Res* 2006; 66:1147-54.

36. Salazar L G, Fikes J, Southwood S, et al. Immunization of cancer patients with HER-2/neu-derived peptides demonstrating high-affinity binding to multiple class II alleles. *Clin Cancer Res* 2003; 9:5559-65.

37. Sotiriadou R, Perez S A, Gritzapis A D, et al. Peptide HER2(776-788) represents a naturally processed broad MHC class II-restricted T cell epitope. *Br J Cancer* 2001; 85:1527-34.

38. Chang C H, Flavell R A. Class II transactivator regulates the expression of multiple genes involved in antigen presentation. *J Exp Med* 1995; 181:765-7.

39. Radosevich M, Jager M, Ono S J Inhibition of MHC class II gene expression in uveal melanoma cells is due to methylation of the CIITA gene or an upstream activator. *Exp Mol Pathol* 2007; 82:68-76.

40. Chen P W, Murray T G, Salgaller M L, Ksander B R. Expression of MAGE genes in ocular melanoma cell lines. *J Immunother* 1997; 20:265-75.

41. van Dinten L C, Pul N, van Nieuwpoort A F, Out C J, Jager M J, van den Elsen P J. Uveal and cutaneous melanoma: shared expression characteristics of melanoma-associated antigens. *Invest Ophthalmol Vis Sci* 2005; 46:24-30.

42. Huang X Q, Mitchell M S, Liggett P E, Murphree A L, Kan-Mitchell J. Non-fastidious, melanoma-specific CD8+ cytotoxic T lymphocytes from choroidal melanoma patients. *Cancer Immunol Immunother* 1994; 38:399-405.

43. Kan-Mitchell J, Liggett P E, Harel W, et al. Lymphocytes cytotoxic to uveal and skin melanoma cells from peripheral blood of ocular melanoma patients. *Cancer Immunol Immunother* 1991; 33:333-40.
44. Maat W, Haasnoot G W, Claas F H, Schalij-Delfos N E, Schreuder G M, Jager M J. HLA Class I and II genotype in uveal melanoma: relation to occurrence and prognosis. *Invest Ophthalmol Vis Sci* 2006; 47:3-6.
45. Nabel G J, Gordon D, Bishop D K, et al Immune response in human melanoma after transfer of an allogeneic class I major histocompatibility complex gene with DNA-liposome complexes. *Proc Natl Acad Sci USA* 1996; 93:15388-93.
46. Danna E A, Sinha P, Gilbert M, Clements V K, Pulaski B A, Ostrand-Rosenberg S. Surgical removal of primary tumor reverses tumor-induced immunosuppression despite the presence of metastatic disease. *Cancer Res* 2004; 64:2205-11.
47. Shankaran V, Ikeda H, Bruce A T, et al. IFNγ and lymphocytes prevent primary tumour development and shape tumour immunogenicity. Nature 2001; 410:1107-11.
48. Svane I M, Engel A M, Nielsen M B, Ljunggren H G, Rygaard J, Werdelin O. Chemically induced sarcomas from nude mice are more immunogenic than similar sarcomas from congenic normal mice. *Eur J Immunol* 1996; 26:1844-50.
49. Tschentscher F, Husing J, Holter T, et al. Tumor classification based on gene expression profiling shows that uveal melanomas with and without monosomy 3 represent two distinct entities. *Cancer Res* 2003; 63:2578-84.
50. Onken M D, Worley L A, Ehlers J P, Harbour J W. Gene expression profiling in uveal melanoma reveals two molecular classes and predicts metastatic death. *Cancer Res* 2004; 64:7205-9.

That which is claimed is:

1. A tumor cell-based vaccine for a recipient comprising: primary immune-privilege tumor cells that constitutively express MHC class I molecules and do not constitutively express MHC class II molecules, wherein the primary immune-privilege tumor cells are genetically modified to express at least one costimulatory molecule, that activates CD4+ T cells, and at least one MHC class II allele, and wherein the MHC class II allele is syngeneic to the recipient, wherein the primary immune-privilege tumor cells are primary ocular melanoma cells.

2. The tumor cell based vaccine according to claim 1, wherein the primary immune-privilege tumor cells do not express Ii.

3. The tumor cell based vaccine according to claim 2, wherein the primary tumor cells are genetically modified by introducing a vector comprising nucleotide sequences encoding for the costimulatory molecule and the at least one MHC class II allele protein.

4. The tumor cell base vaccine according to claim 1, wherein the vaccine comprises at least two different MHC II alleles of the recipient being treated.

5. The tumor cell base vaccine according to claim 3, wherein the costimulatory molecule is CD80.

6. The tumor cell base vaccine according to claim 3, wherein the vector is a recombinant retrovirus.

7. The tumor cell base vaccine according to claim 6, wherein the recombinant retrovirus comprises nucleic acid comprising DNA encoding: (a) at least one MHC class II α chain protein; and (b) at least one MHC class II β chain protein.

8. A method of generating a MHC-II matched allogeneic cell based vaccine that cross reacts with multiple patients and treat metastatic tumors, the method comprising:
   providing primary uveal melanoma cells that arise from ocular immune-privileged tissue;
   determining the HLA-DR type of the primary uveal melanoma cells;
   isolating primary uveal melanoma cells that cannot be induced to express MHC II or Ii;
   transducing the isolated primary uveal melanoma cells with at least one vector comprising nucleic acid encoding for the determined HLA-DR allele or a variant thereof and a co stimulatory molecule or variant thereof to provide modified cells that express the transduced HLA-DR and co stimulatory sequences.

9. The method according to claim 8, wherein the MHC-II matched allogeneic cell based vaccine comprises at least two different MHC II alleles of the subject being treated.

10. The method according to claim 8, wherein the HLA-DR type is HLA-DR1.

11. The method according to claim 8, further determining the HLA-A, B of C type of the primary uveal melanoma cells.

12. The method according to claim 9, wherein vector is a recombinant retrovirus.

13. The method according to claim 12, wherein the recombinant retrovirus comprises nucleic acid comprising DNA encoding: (a) at least one MHC class II α chain protein; and (b) at least one MHC class II β chain protein.

14. An ex vivo method for inducing an increased population of $CD4^+$ T cells in a subject, comprising:
   (a) removing a blood sample from the subject and isolating T-cells;
   (b) determining HLA genotypes of the subject;
   (c) contacting the isolated T-cells with a vaccine comprising:
   a primary ocular melanoma cell that constitutively express MHC class I molecules and does not constitutively express MHC class II molecules and Ii; and is genetically modified to express a co-stimulatory molecule that activates CD4+ T-cells and at least one MHC class II allele, wherein the MHC class II allele is syngeneic to the HLA genotype of the subject; and
   (d) reintroducing the activated T-cells into the subject.

* * * * *

SEQUENCE LISTING

```
<160> NUMBER OF SEQ ID NOS: 10

<210> SEQ ID NO 1
<211> LENGTH: 27
<212> TYPE: DNA
<213> ORGANISM: Artificial Sequence
<220> FEATURE:
<223> OTHER INFORMATION: Synthetic Construct

<400> SEQUENCE: 1
tgtcgctagc atggccataa gtggagt                                       27

<210> SEQ ID NO 2
<211> LENGTH: 30
<212> TYPE: DNA
<213> ORGANISM: Artificial Sequence
<220> FEATURE:
<223> OTHER INFORMATION: Synthetic construct

<400> SEQUENCE: 2
actgctcgag ttacagaggc cccctgcgtt                                    30

<210> SEQ ID NO 3
<211> LENGTH: 28
<212> TYPE: DNA
<213> ORGANISM: Artificial Sequence
<220> FEATURE:
<223> OTHER INFORMATION: Synthetic Construct

<400> SEQUENCE: 3
agtacccggg atggtgtgtc tgaagctc                                      28

<210> SEQ ID NO 4
<211> LENGTH: 29
<212> TYPE: DNA
<213> ORGANISM: Artificial Sequence
<220> FEATURE:
<223> OTHER INFORMATION: Synthetic Construct

<400> SEQUENCE: 4
tgcggccgct cagctcagga atcctgttg                                     29

<210> SEQ ID NO 5
<211> LENGTH: 34
<212> TYPE: DNA
<213> ORGANISM: Artificial Sequence
<220> FEATURE:
<223> OTHER INFORMATION: Synthetic Construct
```

<400> SEQUENCE: 5
gatctcgagc tcctaggaat tgtttggccg aggc                       34

<210> SEQ ID NO 6
<211> LENGTH: 34
<212> TYPE: DNA
<213> ORGANISM: Artificial Sequence
<220> FEATURE:
<223> OTHER INFORMATION: Synthetic Construct

<400> SEQUENCE: 6
agctcgagga tccttaacaa accggctccg ccgg                       34

<210> SEQ ID NO 7
<211> LENGTH: 42
<212> TYPE: DNA
<213> ORGANISM: Artificial Sequence
<220> FEATURE:
<223> OTHER INFORMATION: Synthetic Construct

<400> SEQUENCE: 7
agctgctcga gttaacggat cctaggaagc ttgcggccgc at              42

<210> SEQ ID NO 8
<211> LENGTH: 40
<212> TYPE: DNA
<213> ORGANISM: Artificial Sequence
<220> FEATURE:
<223> OTHER INFORMATION: Synthetic Construct

<400> SEQUENCE: 8
cgatgcggcc gcaagcttcc taggatccgt taactcgagc                 40

<210> SEQ ID NO 9
<211> LENGTH: 867
<212> TYPE: DNA
<213> ORGANISM: Homo sapiens

<400> SEQUENCE: 9
atgggccaca cacggaggca gggaacatca ccatccaagt gtccatacct caatttcttt      60
cagctcttgg tgctggctgg tctttctcac ttctgttcag gtgttatcca cgtgaccaag     120
gaagtgaaag aagtggcaac gctgtcctgt ggtcacaatg tttctgttga agagctggca     180
caaactcgca tctactggca aaaggagaag aaaatggtgc tgactatgat gtctggggac     240
atgaatatat ggcccgagta caagaaccgg accatctttg atatcactaa taacctctcc     300
attgtgatcc tggctctgcg cccatctgac gagggcacat acgagtgtgt tgttctgaag     360
tatgaaaaag acgctttcaa gcgggaacac ctggctgaag tgacgttatc agtcaaagct     420
gacttcccta cacctagtat atctgacttt gaaattccaa cttctaatat tagaaggata     480
atttgctcaa cctctggagg ttttccagag cctcacctct cctggttgga aaatggagaa     540
gaattaaatg ccatcaacac aacagtttcc caagatcctg aaactgagct ctatgctgtt     600
agcagcaaac tggatttcaa tatgacaacc aaccacagct tcatgtgtct catcaagtat     660
ggacatttaa gagtgaatca gaccttcaac tggaatacaa ccaagcaaga gcattttcct     720
gataacctgc tcccatcctg ggccattacc ttaatctcag taaatggaat ttttgtgata     780
tgctgcctga cctactgctt tgccccaaga tgcagagaga aaggaggaa tgagagattg     840 agaagggaaa gtgtacgccc tgtataa                                         867

```
<210> SEQ ID NO 10
<211> LENGTH: 288
<212> TYPE: PRT
<213> ORGANISM: Homo sapiens

<400> SEQUENCE: 10

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
                20                  25                  30

Ser Gly Val Ile His Val Thr Lys Glu Val Lys Glu Val Ala Thr Leu
            35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
                100                 105                 110

Thr Tyr Glu Cys Val Val Leu Lys Tyr Glu Lys Asp Ala Phe Lys Arg
            115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
                180                 185                 190

Pro Glu Thr Glu Leu Tyr Ala Val Ser Ser Lys Leu Asp Phe Asn Met
            195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
                260                 265                 270

Glu Arg Arg Arg Asn Glu Arg Leu Arg Arg Glu Ser Val Arg Pro Val
            275                 280                 285
```